(12) United States Patent
Strelchenok

(10) Patent No.: US 6,403,554 B2
(45) Date of Patent: Jun. 11, 2002

(54) POLYUNSATURATED FATTY ACID DERIVATIVES AND THEIR USE

(75) Inventor: Oleg Strelchenok, Minsk (SE)

(73) Assignee: Ardenia Investments Ltd. (GI)

( * ) Notice: Subject to any disclaimer, the term of this patent is extended or adjusted under 35 U.S.C. 154(b) by 0 days.

(21) Appl. No.: 09/854,064

(22) Filed: May 11, 2001

Related U.S. Application Data

(62) Division of application No. 09/471,105, filed on Dec. 21, 1999, now Pat. No. 6,274,747.

(30) Foreign Application Priority Data

Dec. 23, 1998 (SE) ................................. 9804537
Mar. 16, 1999 (SE) ................................. 9900941

(51) Int. Cl.$^7$ .................... A01K 38/00; A01N 37/18
(52) U.S. Cl. ................... 514/2; 514/8; 514/21; 514/885; 554/36; 554/40; 554/80; 530/350
(58) Field of Search ............. 554/40, 36, 80; 514/2, 8, 21, 885; 530/350

(56) References Cited

PUBLICATIONS

Sheskin et al., "Structural Requirements for Binding of Anandamide–Type Compounds to the Brain Cannabinoid Receptor", J. Med. Chem., vol. 40, pp. 659–667 (1997).

Barua et al., "Preparation of Retinamides by Use of Retinoyl Fluoride", J. of Lipid Research, vol. 26, pp. 258–262 (1985).

J. Med. Chem. 40, (1997), pp. 659–667.

*Primary Examiner*—Deborah Carr
(74) *Attorney, Agent, or Firm*—Morrison & Foerster LLP

(57) ABSTRACT

Novel amides are disclosed, in particular amides of the all-trans-retinoic acid or 13-cis-retinoic acid and arachidonic acid and docosahexaenoic acid and eicosapentaenoic acid or linoleic acid with 2-aminoethanol, alpha-L-serine, alpha-L-threonine, alpha-L-tyrosine containing phosphate groups. Further, the present invention discloses the synthesis and use of these compounds, in particular their pharmaceutical application.

30 Claims, No Drawings

POLYUNSATURATED FATTY ACID DERIVATIVES AND THEIR USE

This is a Divisional application of U.S. patent application Ser. No. 09/471,105 filed Dec. 21, 1999 now U.S. Pat. No. 6,274,747.

FIELD OF THE INVENTION

This invention relates to novel polyunsaturated fatty acid derivatives and their use as therapeutic agents.

BACKGROUND OF THE INVENTION

Amides of fatty acids (saturated and unsaturated) having the following formula:

$$R—CO—NH_2$$

wherein the R is alkyl residue of fatty acid, represent a new group of lipid bioregulators originated from long-chain fatty acids via amidation by corresponding amines. Erucamide (13-docosenamide) was found to be the major bovine mesentery angiogenic lipid. The mechanism of angiogenic activity is unknown and this lipid does not promote proliferation of endothelial cells or induce inflammatory effects (Wakamatsu K. et al., Biochem. Biophys. Res. Commun., V.168. p. 423–429, 1990). A molecule isolated from the cerebrospinal fluid of sleep-deprived cats has been chemically characterized and identified as cis-9,10-octadecenoamide. Other fatty acid primary amides in addition to cis-9,10-octadecenoamide were identified as natural constituents of the cerebrospinal fluid of cat, rat and human, indicating that these compounds compose a distinct family of brain lipids. Synthetic cis-9,10-octadecenoamide induced physiological sleep when injected into rats. Together, these results suggest that fatty acid primary amides may represent a previously unrecognised class of biological signal molecules (Cravatt B. F. et al., Science., V. 268., P.1506–1509, 1995).

A very thoroughly investigated group of compounds are ethanol amides of fatty acids, having the following formula:

$$R—CO—NH—CH_2CH_2—OH$$

where R is an alkyl residue of a fatty acid.

Ethanol amides of fatty acids bound with cannabinoid receptors in the central nervous system or in peripheral tissues are considered as endogenous ligands for these receptors. They exhibit pharmacological patterns like cannabimimetics (Bezuglov V. V. et al. Biochemistry (Moscow). V.63, N 1. P. 27–37,1998).

Amides of retinoic acid (cis-trans isomers) with some amino acids having the following formula:

$$R—CO—NH—Y—COOH$$

wherein R is an alkyl residue of retinoic acid and Y is a residue of amino acid have been synthesised via all-trans-retinoyl chloride and an ester of the amino acid (Shealy Y. F. et al., J.Med.Chem. V.31.,P.190–196, 1988). The retinoyl derivatives of leucine, phenylalanine, alanine, tyrosine and glutamic acid were prepared. The 13-cis-retinoyl derivatives of leucine, phenylalanine, alanine, and glycine were prepared similarly from 13-cis-retinoic acid. In assays of the retynoylamino acids for reversal of squamous metaplasia in hamster trachea organ cultures, these compounds were less active than retinoic acid, but the leucine, alanine and phenylalanine derivatives were similar in activity to several retinamides that suppress bladder carcinogenesis in vivo.

Two of the retinoylamino acids, as well as two simple retinamides were shown to be moderately cytotoxic to murine leukemia and human epidermoid carcinoma cells in culture.

One problem addressed by the present invention is that of making available novel compounds for use in the manufacture of pharmaceuticals, e.g. for the treatment of cancer and immune deficiencies, said compounds exhibiting i.a. higher activity than presently known compounds.

SUMMARY OF THE INVENTION

The present invention makes available novel amides according to the attached claims, in particular amides of the all-trans-retinoic acid or 13-cis-retinoic acid and arachidonic acid and docosahexaenoic acid and eicosapentaenoic acid or linoleic acid with 2-aminoethanol, alpha-L-serine, alpha-L-threonine, alpha-L-tyrosine containing phosphate groups. Further, the present invention discloses the use of these compounds, in particular their pharmaceutical application as specified in the attached claims.

The structure of these compounds is covered by the following general formula:

$$R—CONH—X—OPO(OH)_2$$

wherein
R is

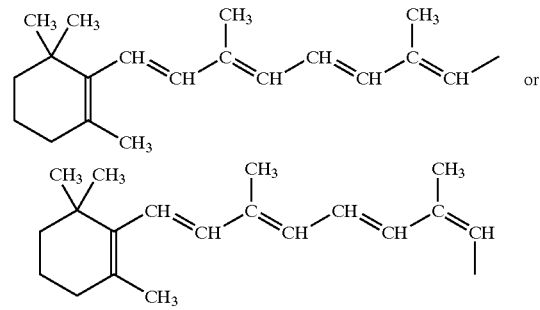

or $CH_3(CH_2)_4(CH=CH—CH_2)_4CH_2CH_2—$
or $CH_3(CH_2CH=CH)_6CH_2CH_2—$
or $CH_3(CH_2CH_2CH=CH)_5(CH_2)_3—$
or $CH_3(CH_2CH=CH)_3(CH_2)_7—$ and X is $—CH_2—CH_2—$
or $—CH(CO_2H)—CH_2—$
or $—CH(CO_2H)—CH(CH_3)—$
or $—CH(CO_2H)—CH_2—C_6H_5—$ Thus the amino group of 2-aminoethanol or the alpha-amino group of amino acid forms an amide bond with the carboxylic group of arachidonic acid, docosahexaenoic acid, eicosapentaenoic acid or linoleic acid and all-trans-retinoic acid or 13-cis retinoic acid. At the same time the hydroxyl group of 2-aminoethanol and the amino acid is modified by a phosphate residue. The compounds can be applied as immunostimulating therapeutical agents for the treatment of immune-deficiencies.

DESCRIPTION OF THE INVENTION

The novel compounds according to the present invention are amides of all-trans-retinoic acid or 13-cis-retinoic acid and arachidonic acid and docosahexaenoic acid and eicosapentaenoic acid or linoleic acid with 2-aminoetanol, alpha-L-serine, alpha-L-threonine, alpha-L-tyrosine. At the same time hydroxyl groups of amino acids and 2-aminoethanol are modified by phosphate residues. The all-trans-retinoic acid or 13-cis retinoic acid and arachidonic acid and docosahexaenoic acid and eicosapentaenoic acid or linoleic acid have been derived by various procedures from naturally-occurring products. It is however possible, within the scope of the present invention, to produce these compound synthetically.

The main characteristic among the novel synthesised compounds is the phosphorylation of the hydroxyl groups of N-acyl derivatives of amino acids and 2-aminoethanol.

Retinoic acid derivatives according to the present invention include the following compounds:

1. N-(all-trans-retinoyl)-o-phospho-2-aminoethanol
1a. N-(13-cis-retinoyl)-o-phospho-2-aminoethanol
2. N-(all-trans-retinoyl)-o-phospho-L-serine
2a. N-(13-cis-retinoyl)-o-phospho-L-serine
3. N-(all-trans-retinoyl)-o-phospho-L-threonine
3a. N-(13-cis-retinoyl)-o-phospho-L-threonine
4. N-(all-trans-retinoyl)-o-phospho-L-tyrosine
4a. N-(13-cis-retinoyl)-o-phospho-L-tyrosine Arachidonic acid derivatives according to the present invention include the following compounds:

5. N-arachidonoyl-o-phospho-2-aminoethanol
6. N-arachidonoyl-o-phospho-L-serine
7. N-arachidonoyl-o-phospho-L-threonine
8. N-arachidonoyl-o-phospho-L-tyrosine Docosahexaenoic acid derivatives according to the present invention include the following compounds:

9. N-docosahexaenoyl-o-phospho-2-aminoethanol
10. N-docosahexaenoyl-o-phospho-L-serine
11. N-docosahexaenoyl-o-phospho-L-threonine
12. N-docosahexaenoyl-o-phospho-L-tyrosine Eicosapentaenoic acid derivatives according to the present invention include the following compounds:

13. N-eicosapentaenoyl-o-phospho-2-aminoethanol
14. N-eicosapentaenoyl-o-phospho-L-serine
15. N-eicosapentaenoyl-o-phospho-L-threonine
16. N-eicosapentaenoyl-o-phospho-L-tyrosine Linoleic acid derivatives according to the present invention include the following compounds:

17. N-linolenoyl-o-phospho-2-aminoethanol
18. N-linolenoyl-o-phospho-L-serine
19. N-linolenoyl-o-phospho-L-threonine
20. N-linolenoyl-o-phospho-L-tyrosine The structural formulas of these compounds are presented below:

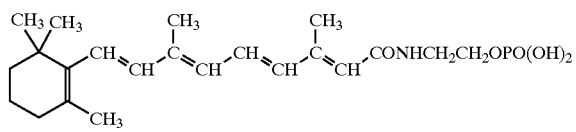

-continued

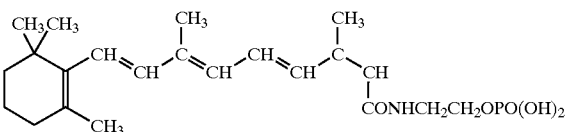

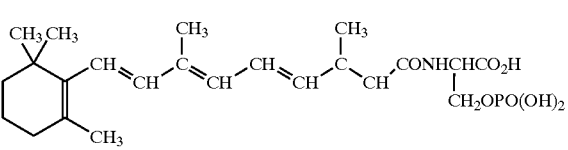

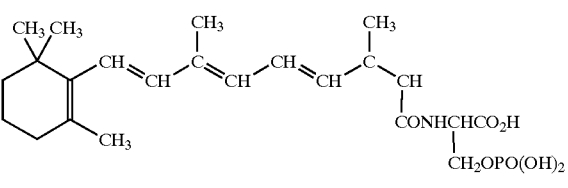

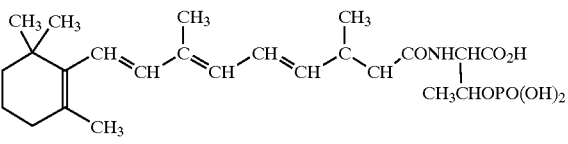

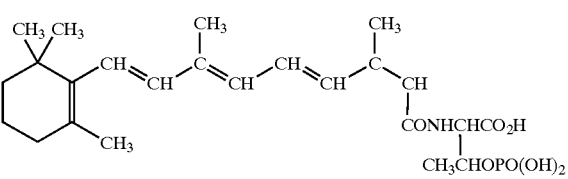

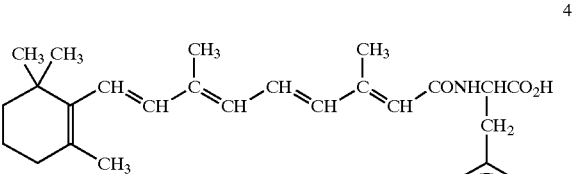

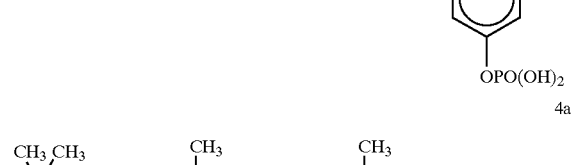

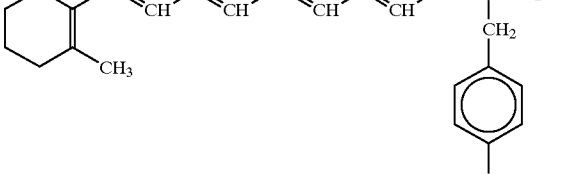

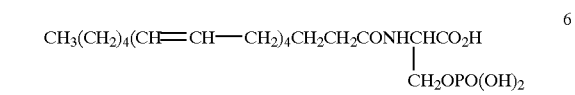

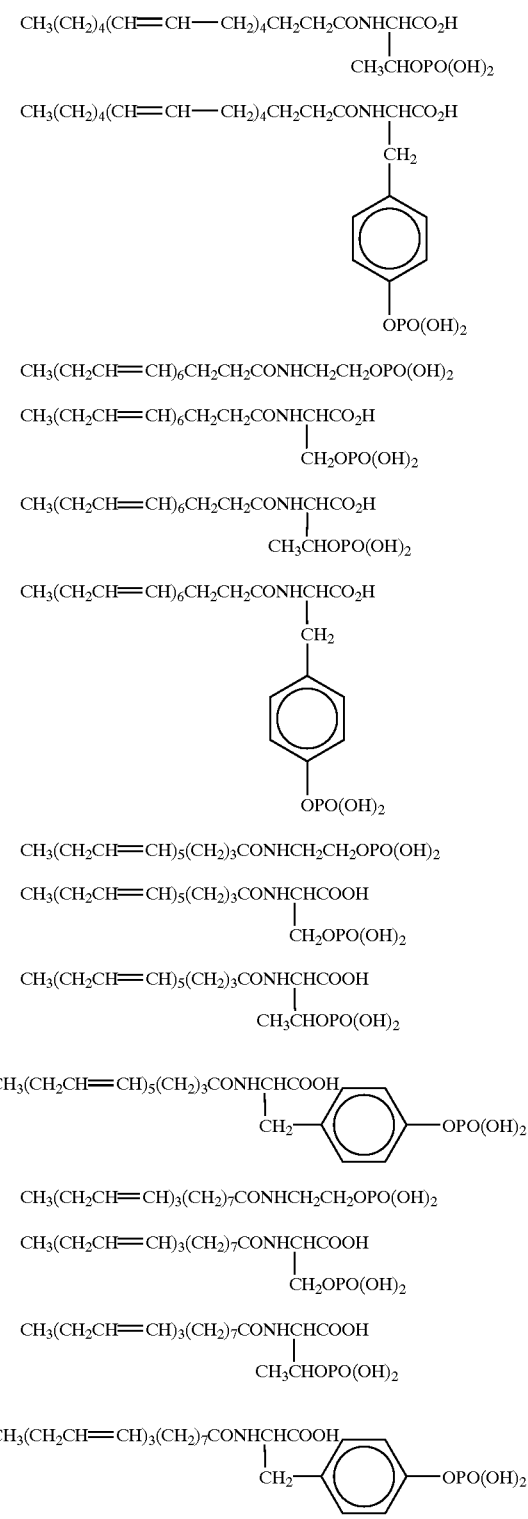

In developing the scheme of synthesis the present inventor took into account the following properties of the title compounds:
i) a high degree of unsaturation
ii) presence of an asymmetric centre
iii) presence of sufficiently labile groups e.g. amide and phosphate.

Many of the well-known methods of acylation and phosphorylation could therefore not be used for the synthesis of such compounds. The preparation of the mixed carbonic carboxylic anhydrides followed by acylation of amino moiety of the methyl esters of hydroxyamino acids and ethanolamine was carried out at low temperature. The method of synthesis developed by the present inventor enables the N-acyl derivatives to be obtained with nearly quantitative yields. It is demonstrated that beta-cyanoethyl phosphate is a universal phosphorylation agent for hydroxyamino acids containing primary, secondary or aromatic OH-groups. Beta-cyanoethyl and ester protective groups were removed simultaneously by mild alkaline hydrolysis (0° C., 1.5 N NaOH). It is worth emphasising that all compounds prepared by this method are formed in good or reasonable yields. In all experiments, the inventor has used synthesised title compounds in the form of ammonia salts.

The molecules of the title compounds have a polar and non-polar part (hydrophilic and hydrophobic in water systems) simultaneously. These long chain molecules are present in water solutions in the form of micelles, if their concentration is equal to the critical micelle concentration or higher. The structural organisation of the title compounds in micelles could be considered as a new organisation level of biological active molecules with specific physiological activity. It shall be noted that the process of micelle formation is reversible.

The influence of the title compounds 1 through 4, 1a through 4a, and 5 through 20 on humoral immune response was estimated by counting the quantity of antibody-forming cells (AFC) in the mice spleen. It has been experimentally proved, that the immunogenic activity of all compounds is dose-dependent. In particular, compounds 8, and 10 through 14, 17, 19 and 20, in doses of 45.5 and 91 μg/mouse exhibit no immunogenic activity, but at the same time in the dose of 136.5 μg/mouse these compounds displayed an immunostimulating action. It was found that the relative amount of AFC on the $5^{th}$ day after injection of compound 10 increased by 138% and the total AFC amount increased by 159%. For compound 11—an increase of 67% and 80%, respectively, was recorded. For compound 12—an increase of 134% and 99% respectively, was recorded. For compound 8—an increase of 31% and 91% respectively, was recorded. For compound 13—an increase of 41% and 49% respectively, was recorded, and for compound 14—an increase of 52% and 51% respectively. For compound 17, the increase was 31% and 30%; for compound 19, 40% and 40%; for compound 20, 49% and 51%, respectively. The increase was calculated as compared with the amount of cells in the animals immunised only with sheep erythrocytes.

Compounds 3, 4, 1a, and 2a, in the doses of 45.5 μg/mouse, exhibit no immunogenic activity. It was found that the relative amount of AFC on the $5^{th}$ day after injection to the animals, for the compound 3, in a dose of 91 and 136.5 μg/mouse, increased by 103% and 136%; and in respect of the total AFC amount an increase of 49%; and, 164%, respectively, was recorded. For compound 4 in a dose of 91 and 136.5 μg/mouse, the relative amount of AFC increased by 70% and 233% and the total AFC amount increased by 45% and 130%, respectively. For compound 1a in a dose of 91 and 136.5 μg/mouse, the relative amount of AFC increased by 29% and 52%, and the total AFC amount increased by 27% and 66%, respectively. For compound 2a in a dose of 91 and 136.5 μg/mouse, the relative amount of AFC increased by 93% and 111%, and the total AFC amount increased by 48% and 71%, respectively. The increase is calculated as a comparison with the amount of cells in animals immunised only with sheep erythrocytes.

The critical micelle concentration (CMC) values for compounds 1 through 4, 1a through 4a were determined as described by Griess W. (Fette Seifen Anstrichmi., 1955. Bd.57, s. 24–32) and for compounds 5 through 20 the CMC values were determined as described by A. Chattopadhyay and E. London (Anal. Biochem., 1984, 139, P.408–412). The CMC-values for ammonia salts of compounds 1 through 4 and 1a through 4a are in the interval of $1 \cdot 10^{-4}$ M–$4 \cdot 10^{-4}$ M and for ammonia salts of compounds 5 through 20, in the interval of $1 \cdot 10^{-3}$ M–$2 \cdot 10^{-3}$ M. That explains why, in the present experiments, compounds 1a, 2a, 3, and 4 display immunostimulating effect in vivo in micelle form at 91 µg/mouse and compounds 8, and 10 through 14, 17, 19 and 20—at 136.5 µg/mouse.

According to the obtained results, the title compounds display immunostimulating effects in vivo resulting in the enhancement of the amount of antibody-forming cells (AFC) in the spleen and in the enhancement of the antibody titres. Some of these compounds induce the conversion of B-lymphocytes to AFC and enhance the production of IgM-antibodies, ensuring a 2 to 3-fold increase of the immune response in C57B1/6 mice which are low-reactive to sheep red blood cells (SRBC).

It is known that one of the factors of genetically determined low reactivity of some lines of mice is insufficient extent of the processes of T- and B-lymphocyte migration and co-operation in immunisation with the particular antigen. Thus, using the studied compounds made it possible to convert genetically low-reacting animals to high-reacting ones. Lymphokines and monokines such as interleukin-1 and -2, thymic hormones, hematopoetin, factor of tumour necrosis, interferons, the molecular weight of which is less then that of albumin, are captured actively by the liver, filtrated by the kidneys, which results in their quick disappearance from the blood stream. The interest attracted by these immunomodulators is not too great due to their low effectiveness and high toxicity. The studied compounds can be promising as potent means for correction of immunity disorders localised at the level of immunocompetent cells, including the possibility of phenotypic correction of the immune response.

Reversible protein phosphorylation is one of the most important mechanisms of regulating intracellular processes such as cell cycle, growth and differentiation (Edelman A. M. et al., A. Rev. Biochem. V. 56., P. 567–613, 1987; Han K.-K., Martinage A., Int. J. Biochem. V. 24. N1.,P. 19–28, 1992). The most common phosphorylated amino acids are serine, threonine and tyrosine (on the hydroxyl group). Calcium and cAMP exert many of their cellular effects by controlling the activity of a protein kinases. Protein kinases catalyse the transfer of phosphate groups from a molecule of adenosine triphosphate (ATP) to other proteins. The addition of a phosphate group alters protein function; indeed, widespread protein phosphorylation is thought to underlie the changes in cell behaviour induced by some extracellular signals. It is contemplated by the present inventor that the title compounds could be such signal molecules.

Alpha-fetoprotein (AFP) forms a reversible equilibrium complex with N-arachidonoyl aminoethylphosphate (N-AAP). The protein is reversiblylinked with to a micelle containing up to 300 molecules of N-AAP (See International Application No PCT/EP99/04201 by the same inventor).

The inventor has now shown that AFP forms reversible equilibrium complexes with all the title compounds of the present invention. These inventive complexes may contain their components in highly varying molar ratios, such as from an equimolar ratio to a significant overabundance of compounds 1 through 4, 1a through 4a, and 5 through 20 in relation to AFP. For compounds 1 through 4, 1a through 4a, and 5 through 20, the inhibition equilibrium association constants ($K_i$) of arachidonic acid with AFP were determined to be in the interval—$0.9 \cdot 10^6$ M$^{-1}$–$4 \cdot 10^6$ M$^{-1}$.

The inventive complexes may be obtained by adding water solution of any titled compound to a water solution of AFP followed by ultrafiltration, said filtration resulting in concentrating the solution and removing any compound (e.g. any one of compounds 1 through 4, 1a through 4a, 5 through 20) that remained unbound to AFP. The AFP concentration in solution varies from 0, 1 to 2 mg/ml and that of the compound from 0,005 up to 30 mg/ml. The changes of molecular weight of the AFP as judged by gel-filtration is an evidence of the existence of AFP complexes with micelles of compounds 1 through 4, 1a through 4a, and 5 through 20.

In one embodiment the molecular weight of AFP incorporated in the complex with the title compound increases by approximately 2 times. Micelles contained about 100–200 lipid molecules. In another embodiment the molecular weight of AFP incorporated in the complex with any one of the compounds 1 through 4, 1a through 4a, and 5 through 20 increases by approximately 2–3 times. The micelles contained 200–300 lipid molecules.

The influence of complexes of AFP with one of the title compounds 1–4, 1a–4a, 5–20 as well as their basic components on humoral immune response was estimated by counting the quantity of antibody-forming cells (AFC) in the mice spleen. In particularly it has been experimentally proved that a compounds 1, 2a, 3 in the dose of 45.5 µg/mouse and a compounds 7, 10, 14, 15 in the dose 91 µg/mouse and human or rat AFP in the dose 9 µg/mouse do not inhibit immunogenic activity.

Administration of a complex of AFP with compound 1 in the dose of 45.5 µg/mouse (complex 1:100) resulted in that the relative amount of AFC increased by 56% and the total AFC amount increased by 43%; for complex AFP with compound 2a in the dose of 45.5 µg/mouse (complex 1:100) the corresponding figures increased by 77% and 43% accordingly; for a complex APP with compound 3 in the dose of 45.5 µg/mouse (complex 1:100) the corresponding figures increased by 76% and 48% accordingly in comparison with the amount of cells in animals immunized only with sheep erythrocytes.

Administration of a complex of AFP with compound 7 in the dose of 91 µg/mouse (complex 1:200) resulted in that the relative amount of AFC increased by 49% and the total AFC amount increased by 47%; for complex AFP with compound 10 in the dose of 91 µg/mouse (complex 1:200) the corresponding figures increased by 88% and 79% accordingly; for a complex AFP with compound 14 in the dose of 91 µg/mouse (complex 1:200) the corresponding figures increased by 55% and 53% accordingly; for a complex AFP with compound 15 in the dose of 91 µg/mouse (complex 1:200) the corresponding increased by 50% and 48%, respectively. The increase is calculated as a comparison with the amount of cells in animals immunised only with sheep erythrocytes.

All title compounds in the form of complexes with AFP exhibit the immunostimulating effect in vivo in lower concentrations than these compounds alone. It is suggested, taht AFP reduces the critical micelle concentration (CMC) of the title compounds on account of highly cooperative specific interactions in complexes comprising AFP and a ligand. So, in the experiments performed by the inventor, compounds 1, 2a, and 3 in a complex with AFP displayed an immunostimulating effect in vivo at a dose of 45.5 µg/mouse and compounds 7, 10, 14, and 15—at a dose of 91 µg/mouse.

In the experiments disclosed in the present application, the inventor has used C57B1/6 mice, which are low reactive to sheep red blood cells (SRBC). It possible, that complexes title compounds 1–4, 1a–4a, and 5–20 with AFP would display immunostimulating effect at more low amounts, if mice, which are high reactive to SRBC, have been used. The present inventor has shown that complex compound 5 (N-AAP) with AFP displays immunostimulating effect at 45.5 µg/mouse, in experiments with CBA mice (See the International Application No PCT/EP99/04201).

AFP was isolated from human cord blood by immunoaffinity chromatography on monoclonal antibodies against AFP immobilised on Sepharose® immunoaffinity chromatography on polyclonal antibodies to the proteins of normal human blood and gel-filtration on Sephacryl S-200®. The AFP preparation thus obtained exhibited a purity above 99% and did not contain low molecular weight impurities and retained completely its biological activity.

Rat AFP was isolated from neonatal rat serum. Monospecific anti-rat serum alfa-fetoprotein IgG was coupled to cyanogen bromide-activated Sepharose® 4B (4.5 mg/ml packed volume of gel) to yield an immunoaffinity matrix. Acidic elution conditions were as described previously (Calvo M., et al., J.Chromatogr. Vol.328, p. 392–395, 1985).

Other sources of AFP may be purified and/or modified AFP from other mammals, for example from genetically modified mammals, or from cell cultures. Preferably, the AFP is biotechnologically manufactured using a cell culture of genetically modified cells expressing human AFP. With knowledge of the nucleotide sequence coding for human AFP, this can be inserted in a host, together with necessary promoters and other sequence information, for example sequences influencing the extracelluar expression of AFP. The AFP is collected from the cell culture and purified by chromatography and may be further purified by gel-filtration. In any case the production method must involve steps, which guarantee that the final product is free from pyrogens and possible viral or bacterial contaminants. Suitable production methods can for example be found in the field of interferon production.

The novel retinoids according to the present invention exhibit good solubility in water due to the presence of the phosphate groups in the molecules. The water solubility opens many opportunities for obtaining various medical forms of the preparations possessing suitable properties for transdermal and/or oral absorption.

The compounds according to the invention can be used as such or as components in pharmaceutical compositions. The compounds can be given systemically or locally, for example topically. Suitable modes of administration of the compounds include intravenous administration, intraperitoneal administration, as well as oral, rectal and transdermal administration. The intended mode of administration is naturally taken into account in the preparation of the final pharmaceutical composition. Normal pharmaceutical adjuvants can naturally be used and the compounds can be made available in the form of injectable solutions, ointments, capsules or tablets, in the form of transdermal patches or suppositories according to the intended use and/or mode of administration.

The therapeutic effective doses for intravenous administration of the title compounds are in intervals:
Compounds 1, 1a, 5, 9, 13, 17: from 5 mg/kg to 10 mg/kg
Compounds 2, 2a, 3, 3a, 6, 7, 10, 11, 14, 15, 18, 19: from 5 mg/kg to 20 mg/kg
Compounds 4, 4a, 8, 12, 16, 20: from 5 mg/kg to 30 mg/kg The therapeutic effective doses for intravenous administration complexes of AFP with title compounds are in intervals:
Compounds 1, 1a, 5, 9, 13, 17: from 2 mg/kg to 10 mg/kg
AFP: from 0.2 mg/kg to 1 mg/kg
Compounds 2, 2a, 3, 3a, 6, 7, 10, 11, 14, 15, 18, 19: from 2 mg/kg to 20 mg/kg
AFP: from 0.2 mg/kg to 2 mg/kg
Compounds 4, 4a, 8, 12, 16, 20: from 2 mg/kg to 30 mg/kg
AFP: from 0.2 mg/kg to 3 mg/kg

EXAMPLES

Materials and Methods

L-Serine, L-threonine, L-tyrosine, and arachidonic, eicosapentaenoic, linoleic, docosahexaenoic and retinoic acids were purchased from Sigma Chemical Co. Ethanolamine, N,N'-dicyclohexylcarbodiimide, and 2-cyanoethyl phosphate barium salt were obtained from Aldrich Chemical Co. Tetrahydrofuran, acetonitrile and pyridine were dried by heating, under reflux, with $CaH_2$ for 3–5 h; these solvents were then distilled at atmospheric pressure and stored over molecular sieves (no. 4A).

The barium salt of 2-cyanoethyl phosphate was converted into the pyridinium salt by passage through a column of Dowex-50 resin (pyridinium form). The eluate was evaporated and the salt was dried by repeated evaporation of added portions of dry pyridine.

$^1$H-NMR spectra at 200 MHz were obtained with a Brucker spectrometer AC-200; tetramethylsilane was used as an internal standard.

Merck silica gel 60 pre-coated plates, which were developed in solvent system A [benzene-dioxan-acetic acid (25:5:1 v/v/v)] and solvent system B [chloroform-methanol-$NH_3$aq (9:7:2 v/v/v)] were used for thin-layer chromatography (TLC). Detection of the compounds on TLC plates was by spraying with 10% sulphuric acid in methanol or with molybdate spray. Flash chromatography was performed on silica gel 60 (230–400 mesh).

Example 1

Synthesis of the N-(cis-5,8,11,14-eicosatetraenoyl)-O-phospho-2-aminoethanol (N-arachidonoyl-O-phospho-2-aminoethanol) (5)

Arachidonic acid (152 mg, 0.5 mmol) and triethylamine (52 mg, 0.51 mmol) were dissolved in 3 ml of dry acetonitrile and chilled to −15° C., and 70 mg (0.51 mmol) of butyl chloroformate was added. After 30 min, the mixture free of the precipitated triethylamine hydrochloride was pipetted in a solution of 2-aminoethanol (61 mg, 1 mmol) in 1 ml of methanol, stirring was continued for 15 min at −15° C., then the mixture obtained was allowed to warm to room temperature. After 2 h, 0.5 M HCl was added, and the mixture was extracted with ether (20 ml). The extract was washed with water, then dried with $Na_2SO_4$, and evaporated under reduced pressure. The residue was dissolved in 2 ml of chloroform and purified by column (2×2 cm) chromatography on aluminum oxide (basic, Brockmann II). Elution of the column with chloroform-methanol (9:1 v/v) and evaporation of the appropriate fractions gave 165 mg (95%) of desired N-arachidonoylaminoethan-2-ol as oil: TLC (system A) $R_f$ 0.4.

A solution of pyridinium cyanoethylphosphate (2 mmol) in anhydrous pyridine (3 ml) was added to dry N-acylaminoethan-2-ol. N,N'-Dicyclohexylcarbodiimide (413 mg, 2 mmol) was then added and the mixture was stirred at room temperature. After 20 h, the mixture was cooled to 0° C., water (0.5 ml) was added and, after stirring for 30 min at room temperature, the precipitated N,N'-dicyclohexylurea was separated by filtration. The filtrate was evaporated under reduced pressure and the residue obtained was fractionated by short column chromatography on silica gel. The desired phosphorylated N-acylaminoalcohol was eluted from column with chloroform-methanol (70–60:30–40, v/v). The composition of the eluates was controlled by TLC on Silica gel 60 plates (system B) using a molybdate spray for detecting the spots. The appropriate fractions were combined, evaporated to dryness in vacuo and residue was dissolved in 1 ml tetrahydrofuran. That solution was added, dropwise over a period of 5 min, to a cooled (ice-bath), stirred 1.5 M NaOHaq (4 ml). After a further 25 min, the mixture was acidified with 1 N HCl to pH 2–3 and extracted with chloroform-methanol (2:1, v/v). The extract was washed with methanol-water (10:9, v/v), concentrated in vacuo and applied to a column of silica gel. The desired product was eluted from column with chloroform-methanol (30–20:70–80, v/v), the fractions containing pure substance stained on the TLC plates with molybdate spray were combined and evaporated to dryness to give 88 mg (41%) of (5): $R_f$ 0.10–0.15 (system B); $^1$H-NMR (CD$_3$SOCD$_3$, 200 MHz) δ0.9–1.0 (t, 3H, ω-CH$_3$); 1.3 (s, 8H, 4CH$_2$); 2.0–2.4 (m, 6H, 2CH$_2$CH=CH and CH$_2$CO); 2.7–2.9 (br s, 6H, 3HC=CHCH$_2$CH=CH); 3.4–3.5 (br s, 2H, CH$_2$NH); 3.9–4.0 (br s, 2H, CH$_2$OP); 5.2–5.4 (br s, 8H, 4HC=CH); 8.2–8.4 (m, 3H, NH and 2POH).

Example 2
Synthesis of the N-(cis-4,7,10,13,16,19-docosahexaenoyl)-O-phospho-2-aminoethanol (9)

This compound was prepared as described above for (5), using 0.5 mmol (164 mg) of cis-4,7,10,13,16,19-docosahexaenoic acid; yield 99 mg (44%); $R_f$ 0.10–0.15 (system B); $^1$H NMR (CD$_3$SOCD$_3$, 200 MHz) δ0.9–1.0 (t, 3H, ω-CH$_3$); 2.0–2.1 (t, 2H, CH$_2$CO); 2.2–2.4 (m, 4H, 2CH$_2$CH=CH); 2.7–2.9 (br s, 10H, 5HC=CHCH$_2$CH=CH); 3.4–3.5 (br s, 2H, CH$_2$NH); 3.9–4.0 (br s, 2H, CH$_2$OP); 5.2–5.4 (br s, 12H, 6HC=CH); 8.2–8.4 (m, 3H, NH and 2POH).

Example 3
Synthesis of the N-(all-trans-Retinoyl)-O-phospho-2-aminoethanol (1)

all-trans-Retinoic acid (150 mg, 0.5 mmol) and triethylamine (52 mg, 0.51 mmol) were dissolved in 1 ml of dry tetrahydrofuran, whereupon dry acetonitrile (2 ml) was added, and the mixture was chilled to –15° C. All further procedures were carried out as described above for (5); yield 59 mg,(28%); $R_f$ 0.10–0.15 (system B); $\lambda_{max}$ (ethanol) 345 nm; $^1$H-NMR (CD$_3$SOCD$_3$, 200 MHz) δ1.0 (s, 6H, 3CH$_2$, ring); 1.4–2.4 (m, 15H, 5CH$_3$); 3.4–3.5 (br s, 2H, CH$_2$NH); 3.9–4.0 (br s, 2H, CH$_2$OP); 5.8–7.0 (m, 6H, 6HC=C); 8.2–8.4 (m, 3H, NH and 2POH)

Example 4
Synthesis of the N-(cis-5,8,11,14-eicosatetraenoyl)-O-phospho-L-serine (N-arachidonoyl-O-phospho-L-serine) (6)

Arachidonic acid (152 g, 0.5 mmol) and triethylamine (52 mg, 0.51 mmol) were dissolved in 3 ml of dry acetonitrile and chilled to –15° C., and 70 mg (0.51 mmol) of butyl chloroformate was added. After 30 min, the mixture free of the precipitated triethylamine hydrochloride was pipetted in a solution of L-serine methyl ester hydrochloride (156 mg, 1 mmol) and 0.14 ml of triethylamine in 1 ml of methanol, stirring was continued for 15 min at –15° C., then that mixture was allowed to warm to room temperature. After 2 h, 0.5 M HCl was added, and the mixture was extracted with ether (20 ml). The extract was washed with water, then dried with Na$_2$SO$_4$, and evaporated in vacuo. The residue was dissolved in 2 ml of chloroform and purified by column (2×2 cm) chromatography on aluminum oxide (basic, Brockmann II). Elution of the column with chloroform-methanol (9:1 v/v) and evaporation of the appropriate fractions gave 186 mg (95%) of desired N-arachidonoyl-L-serine methyl ester as oil: TLC (system A) $R_f$ 0.5.

A solution of pyridinium cyanoethylphosphate (2 mmol) in anhydrous pyridine (3 ml) was added to dry N-arachidonoyl-L-serine methyl ester. N,N'-Dicyclohexylcarbodiimide (413 mg, 2 mmol) was then added and the mixture was stirred at room temperature. After 20 h, the mixture was cooled to 0° C., water (0.5 ml) was added and, after stirring for 30 min at room temperature, the precipitated N,N'-dicyclohexylurea was separated by filtration. The filtrate was evaporated in vacuo and the residue obtained was fractionated by short column chromatography on silica gel. The desired phosphorylated N-arachidonoyl-L-serine methyl ester was eluted from column with chloroform-methanol (30–40:70–60, v/v). The composition of the eluates was controlled by TLC on Silica gel 60 plates (system B) using a molybdate spray for detecting the spots. The appropriate fractions were combined, evaporated to dryness in vacuo and residue was dissolved in 1 ml tetrahydrofuran. The solution obtained was added, dropwise over a period of 5 min, to a cooled (ice-bath), stirred 1.5 M NaOHaq (4 ml). After a further 25 min, the mixture was acidified with 1 N HCl to pH 2–3 and extracted with chloroform-methanol (70–60:30–40, v/v). The extract was washed with methanol-water (10:9, v/v), concentrated in vacuo and applied to a column of silica gel. The desired product was eluted from column with chloroform-methanol (30–20:70–80, v/v), the fractions containing pure substance stained on the TLC plates with molybdate spray were combined and evaporated to dryness to give 82 mg (35%) of (6): $R_f$ 0.05–0.10 (system B); $^1$H-NMR (CD$_3$SOCD$_3$, 200 MHz) δ0.9–1.0 (t, 3H, ω-CH$_3$); 1,3 (s, 8H, 4CH$_2$); 2.0–2.4 (m, 6H, 2CH$_2$CH=CH and CH$_2$CO); 2.7–2.9 (br s, 6H, 3HC=CHCH$_2$CH=CH); 3.9–4.0 br s, 2H, CH$_2$OP); 4.3–4.4 (m, 1H, NHCHCO); 5.2–5.4 (br s, 8H, 4HC=CH); 8.2–8.4 (m, 3H, NH and 2POH)

Example 5
Synthesis of the N-(cis-5,8,11,14-eicosatetraenoyl)-O-phospho-L-threonine (N-arachidonoyl-O-phospho-L-threonine) (7)

This compound was prepared as described above for (6) using 1 mmol (170 mg) of L-threonine methyl ester hydrochloride; yield 97 mg, (40%); $R_f$ 0.05–0.10 (system B); $^1$H-NMR (CD$_3$SOCD$_3$, 200 MHz) δ0.9–1.0 (t, 3H, ω-CH$_3$); 1.2–1.4 (m, 11H, 4CH$_2$ and CH$_3$CHOP); 2.0–2.4 (m, 6H, 2CH$_2$CH=CH and CH$_2$CO); 2.7–2.9 (br s, 6H, 3HC=CHCH$_2$CH=CH); 4.1–4.3 (m, 2H, 2CH) 5.2–5.4 (br s, 8H, 4HC=CH); 8.2–8.4 (m, 3H, NH and 2POH)

Example 6
Synthesis of the N-(cis-4,7,10,13,16,19-docosahexaenoyl)-O-phospho-L-serine (10)

This compound was prepared as described above for (6) using 0.5 mmol (164 mg) of cis-4,7,10,13,16,19-docosahexaenoic acid; yield 91 mg (37%); $R_f$ 0.05–0.10 (system B); $^1$H-NMR (CD$_3$SOCD$_3$, 200 MHz) δ0.9–1.0 (t, 3H, ω-CH$_3$); 2.0–2.1 (t, 2H, CH$_2$CO); 2.2–2.4 (m, 4H, 2CH$_2$CH=CH); 2.7–2.9 (br s, 10H, 5HC=CHCH$_2$CH=CH); 3.9–4.0 (br s, 2H, CH$_2$OP); 4.3–4.4 (m, 1H, NHCHCO); 5.2–5.4 (br s, 12H, 6HC=CH); 8.2–8.4 (m, 3H, NH and 2POH)

Example 7

Synthesis of the N-(cis-4,7,10,13,16,19-docosahexaenoyl)-O-phospho-L-threonine (11)

This compound was prepared as described above for (6) using 0.5 mmol (164 mg) of cis-4,7,10,13,16,19-docosahexaenoic acid and 1 mmol (170 mg) of L-threonine methyl ester hydrochloride; yield 109 mg, (43%); R$_f$ 0.05–0.10 (system B); $^1$H-NMR (CD$_3$SOCD$_3$, 200 MHz) δ0.9–1.0 (t, 3H, ω-CH$_3$); 1.2–1.4 (3H, d, CH$_3$CHOP); 2.0–2.1 (t, 2H, CH$_2$CO); 2.2–2.4 (m, 4H, 2CH$_2$CH=CH); 2.7–2.9 (br s, 10H, 5HC=CHCH$_2$CH=CH); 4.1–4.3 (m, 2H, 2CH); 5.2–5.4 (br s, 12H, 6HC=CH); 8.2–8.4 (m, 3H, NH and 2POH)

Example 8

Synthesis of the N-(all-trans-Retinoyl)-O-phospho-L-serine (2)

all-trans-Retinoic acid (150 mg, 0.5 mmol) and triethylamine (52 mg, 0.51 mmol) were dissolved in 1 ml of dry tetrahydrofuran, then dry acetonitrile (2 ml) was added, and the mixture was chilled to −15° C. All further procedures were carried out as described for (6); yield 56 mg, (24%); R$_f$ 0.05–0.10 (system B); λ$_{max}$ (ethanol) 345 nm; $^1$H-NMR (CD$_3$SOCD$_3$, 200 MHz) δ1.0 (s, 6H, 3CH$_2$, ring); 1.4–2.4 (m, 15H, 5CH$_3$); 3.9–4.0 (br s, 2H, CH$_2$OP); 4.3–4.4 (m, 1H, NHCHCO); 5.8–7.0 (m, 6H, 6HC=C); 8.2–8.4 (m, 3H, NH and 2POH)

Example 9

Synthesis of the N-(all-trans-Retinoyl)-O-phospho-L-threonine (3)

all-trans-Retinoic acid (150 mg, 0.5 mmol) and triethylamine (52 mg, 0.51 mmol) were dissolved in 1 ml of dry tetrahydrofuran, then dry acetonitrile (2 ml) was added, and the mixture was chilled to −15° C. All further procedures were carried out as described for (6) using 1 mmol (170 mg) of L-threonine methyl ester hydrochloride; yield 65 mg, (27%); R$_f$ 0.05–0.10 (system B); λ$_{max}$ (ethanol) 345 nm; $^1$H-NMR (CD$_3$SOCD$_3$, 200 MHz) δ1.0 (s, 6H, 3CH$_2$, ring); 1.2–1.4 (d, 3H, CH$_3$CHOP); 1.4–2.4 (m, 15H, 5CH$_3$); 4.1–4.3 (m, 2H, 2CH); 5.8–7.0 (m, 6H, 6HC=C); 8.2–8.4 (m, 3H, NH and 2POH)

Example 10

Synthesis of the N-(cis-5,8,11,14-eicosatetraenoyl)-O-phospho-L-tyrosine (N-arachidonoyl-O-phospho-L-tyrosine) (8)

Arachidonic acid (152 g, 0.5 mmol) and triethylamine (52 mg, 0.51 mmol) were dissolved in 3 ml of dry acetonitrile and chilled to −15° C., and 70 mg (0.51 mmol) of butyl chloroformate was added. After 30 min, the mixture free of the precipitated triethylamine hydrochloride was pipetted in a solution of tyrosine methyl ester hydrochloride (232 mg, 1 mmol) and 0.14 ml of triethylamine in 1 ml of methanol, stirring was continued for 15 min at −15° C., then the mixture obtained was allowed to warm to room temperature. After 2 h, 0.5 M HCl was added, and the mixture was extracted with ether (20 ml). The extract was washed with water, then dried with Na$_2$SO$_4$, and evaporated in vacuo. The residue was dissolved in 2 ml of chloroform and purified by column (2×2 cm) chromatography on aluminum oxide (basic, Brockmann II). Elution of the column with chloroform-methanol (9:1 v/v) and evaporation of the appropriate fractions gave 222 mg (95%) of desired N-arachidonoyl-L-tyrosine methyl ester as oil: TLC (system A) R$_f$ 0.6.

A solution of pyridinium cyanoethylphosphate (2 mmol) in anhydrous acetonitrile (3 ml) was added to dry N-arachidonoyl-L-tyrosine methyl ester. N,N'-Dicyclohexylcarbodiimide (413 mg, 2 mmol) was then added and the mixture was stirred at room temperature. After 5 days, the mixture was cooled to 0° C., water (0.5ml) was added and, after stirring for 30 min at room temperature, the precipitated N,N'-dicyclohexylurea was separated by filtration. The filtrate was evaporated in vacuo and the residue obtained was fractionated by short column chromatography on silica gel. The desired phosphorylated N-acyl-L-tyrosine methyl ester was eluted from column with chloroform-methanol (70–60:30–40, v/v). The composition of the eluates was controlled by TLC on Silica gel 60 plates (system B) using a molybdate spray for detecting the spots. The appropriate fractions were combined, evaporated to dryness in vacuo and residue was dissolved in 1 ml tetrahydrofuran. The solution obtained was added, dropwise over a period of 5 min, to a cooled (ice-bath), stirred 1.5 M NaOHaq (4 ml). After a further 25 min, the mixture was acidified with 1 N HCl to pH 2–3 and extracted with chloroform-methanol (2:1, v/v). The extract was washed with methanol-water (10:9, v/v), concentrated in vacuo and applied to a column of silica gel. The desired products was eluted from column with chloroform-methanol (30–20:70–80, v/v), the fractions containing pure substance stained on the TLC plates with molybdate spray were combined and evaporated to dryness to give 63 mg (23%) of (8): R$_f$ 0.05–0.10 (system B); $^1$H-NMR (CD$_3$SOCD$_3$, 200 MHz) δ0.9–1.0 (t, 3H, ω-CH$_3$); 1.3 (s, 8H, 4CH$_2$); 2.0–2.4 (m, 6H, 2CH$_2$CH=CH and CH$_2$CO); 2.7–2.9 (br s, 6H, 3HC=CHCH$_2$CH=CH); 2.9–3.1 (m, 2H, CH$_2$Ar); 4.3–4.4 (m, 1H, NHCHCO); 5.2–5.4 (br s, 8H, 4HC=CH); 7.0–7.2 (q, 4H, Ar); 8.2–8.4 (m, 3H, NH and 2POH)

Example 11

Synthesis of the N-(cis-4,7,10,13,16,19-docosahexaenoyl)-O-phospho-L-tyrosine (12)

This compound was prepared as described above for (8) using 0.5 mmol (164 mg) of cis-4,7,10,13,16,19-docosahexaenoic acid; yield 74 mg, (26%); R$_f$ 0.05–0.10 (system B); $^1$H-NMR (CD$_3$SOCD$_3$, 200 MHz) δ0.9–1.0 (t, 3H, ω-CH$_3$); 2.0–2.1 (t, 2H, CH$_2$CO); 2.2–2.4 (m, 4H, 2CH$_2$CH=CH); 2.7–2.9 (br s, 10H, 5HC=CHCH$_2$CH=CH); 2.9–3.1 (m, 2H, CH$_2$Ar); 4.3–4.4 (m, 1H, NHCHCO); 5.2–5.4 (br s, 12H, 6HC=CH); 7.0–7.2 (q, 4H, Ar); 8.2–8.4 (m, 3H, NH and 2POH)

Example 12

Synthesis of the N-(all-trans-Retinoyl)-O-phospho-L-tyrosine (4)

all-trans-Retinoic acid (150 mg, 0.5 mmol) and triethylamine (52 mg, 0.51 mmol) were dissolved in 1 ml of dry tetrahydrofuran, then dry acetonitrile (2 ml) was added, and the mixture was chilled to −15° C. All further procedures were carried out as described for (8) using 1 mmol (232 mg) of L-tyrosine methyl ester hydrochloride; yield 52 mg, (19%); R$_f$ 0.05–0.10 (system B); λ$_{max}$ (ethanol) 345 nm; $^1$H-NMR (CD$_3$SOCD$_3$, 200 MHz) δ1.0 (s, 6H, 3CH$_2$, ring); 1.4–2.4 (m, 15H, 5CH$_3$); 2.9–3.1 (m, 2H, CH$_2$Ar); 4.3–4.4 (m, 1H, NHCHCO); 5.8–7.0 (m, 6H, 6HC=C); 7.0–7.2 (q, 4H, Ar); 8.2–8.4 (m, 3H, NH and 2POH)

Example 13
Synthesis of the N-(13cis-Retinoyl)-O-phospho-2-aminoethanol (1a)

This compound was prepared as described above for (1) using 0.5 mmol (150 mg) of 13-cis-retinoic acid; yield 63 mg, (30%); $R_f$ 0.10–0.15 (system B); $\lambda_{max}$ (ethanol) 347 nm; $^1$H-NMR (CD$_3$SOCD$_3$, 200 MHz) $\delta$1.0 (s, 6H, 3CH$_2$, ring); 1.1–2.2 (m, 15H, 5CH$_3$); 3.3–3.4 (br s, 2H, CH$_2$NH); 3.8–3.9 (br s, 2H, CH$_2$ OP); 5.8–7.0 (m, 6H, 6HC=C); 8.2–8.4 (m, 3H, NH and 2POH)

Example 14
Synthesis of the N-(13-cis-Retinoyl)-O-phospho-L-serine (2a)

This compound was prepared as described above for (2) using 0.5 mmol (150 mg) of 13-cis-Retinoic acid; yield 54 mg, (23%); $R_f$ 0.05–0.10 (system B); $\lambda_{max}$ (ethanol) 347 nm; $^1$H-NMR (CD$_3$SOCD$_3$, 200 MHz) $\delta$1.0 (s, 6H, 3CH$_2$, ring); 1.1–2.2 (m, 15H, 5CH$_3$); 3.8–3.9 (br s, 2H, CH$_2$OP); 4.2–4.3 (m, 1H, NH CH CO); 5.8–7.0 (m, 6H, 6HC=C); 8.2–8.4 (m, 3H, NH and 2POH)

Example 15
Synthesis of the N-(13-cis-Retinoyl)-O-phospho-L-threonine (3a)

This compound was prepared as described above for (3) using 0.5 mmol (150 mg) of 13-cis-Retinoic acid; yield 70 mg, (29%); $R_f$ 0.05–0.10 (system B); $\lambda_{max}$ (ethanol) 347 nm; $^1$H-NMR (CD$_3$SOCD$_3$, 200 MHz) $\delta$1.0 (s, 6H, 3CH$_2$, ring); 1.1–2.2 (m, 18H, 6CH$_3$); 4.1–4.3 (m, 2H, 2CH); 5.8–7.0 (m, 6H, 6HC=C); 8.2–8.4 (m, 3H, NH and 2POH)

Example 16
Synthesis of the N-(13-cis-Retinoyl)-O-phospho-L-tyrosine (4a)

This compound was prepared as described above for (4) using 0.5 mmol (150 mg) of 13-cis-Retinoic acid; yield 54 mg, (20%); $R_f$ 0.05–0.10 (system B); $\lambda_{max}$ (ethanol) 347 nm; $^1$H-NMR (CD$_3$SOCD$_3$, 200 MHz) $\delta$1.0 (s, 6H, 3CH$_2$, ring); 1.1–2.2 (m, 15H, 5CH$_3$); 2.9–3.1 (m, 2H, CH$_2$Ar); 4.2–4.3 (m, 1H, NH CH CO); 5.8–7.0 (m, 6H, 6HC=C); 7.1 (s, 4H, Ar); 8.2–8.4 (m, 3H, NH and 2POH)

Example 17
Synthesis of the N-(cis-5,8,11,14,17-eicosapentaenoyl)-O-phospho-2-aminoethanol (13)

This compound was prepared as described above for (5) using 0.5 mmol (151 mg) of cis-5,8,11,14,17-eicosapentaenoic acid; yield 98 mg, (46%); $R_f$ 0.10–0.15 (system B); $^1$H-NMR (CD$_3$SOCD$_3$, 200 MHz) $\delta$0.9–1.0 (t, 3H, $\omega$-CH$_3$); 1.5–1.6 (t, 2H, CH$_2$); 2.0–2.2 (m, 6H, CH$_2$CO and 2CH$_2$CH=CH); 2.7–2.9 (br s, 8H, 4HC=CH—CH$_2$—CH=CH); 3.2–3.3 (br s, 2H, CH$_2$NH); 3.8–3.9 (br s, 2H, CH$_2$OP); 5.2–5.4 (br s, 10H, 5 HC=CH); 8.2–8.4 (m, 3H, NH and 2POH)

Example 18
Synthesis of the N-(cis-5,8,11,14,17-eicosapentaenoyl)-O-phospho-L-serine (14)

This compound was prepared as described above for (6) using 0.5 mmol (151 mg) of cis-5,8,11,14,17-eicosapentaenoic acid; yield 84 mg, (36%); $R_f$ 0.05–0.10 (system B); $^1$H-NMR (CD$_3$SOCD$_3$, 200 MHz) $\delta$0.9–1.0 (t, 3H, $\omega$-CH$_3$); 1.5–1.6 (t, 2H, CH$_2$); 2.0–2.2 (m, 6H, CH$_2$CO and 2 CH$_2$CH=CH); 2.7–2.9 (br s, 8H, 4HC=CH—CH$_2$—CH=CH); 3.9–4.0 (br s, 2H, CH$_2$OP); 4.34.4 (m, 1H, NH CHCO); 5.2–5.4 (br s, 10H, 5 HC=CH); 8.2–8.4 (m, 3H, NH and 2POH)

Example 19
Synthesis of the N-(cis-5,8,11,14,17-eicosapentaenoyl)-O-phospho-L-threonine (15)

This compound was prepared as described above for (6), using 0.5 mmol (151 mg) of cis-5,8,11,14,17-eicosapentaenoic acid and 1 mmol (170 mg) of L-threonine methyl ester hydrochloride; yield 99 mg, (41%); $R_f$ 0.05–0.10 (system B); $^1$H-NMR (CD$_3$SOCD$_3$, 200 MHz) $\delta$0.9–1.0 (t, 3H, $\omega$-CH$_3$); 1.2–1.4 (d, 3H, CH$_3$CHOP); 1.5–1.6 (t, 2H, CH$_2$); 2.0–2.2 (m, 6H, CH$_2$CO and 2CH$_2$CH=CH); 2.7–2.9 (br s, 8H, 4HC=CH—CH$_2$—CH=CH); 4.1–4.3 (m, 2H, 2CH); 5.2–5.4 (br s, 10H, 5HC=CH); 8.2–8.4 (m, 3H, NH and 2POH)

Example 20
Synthesis of the N-(cis-5,8,11,14,17-eicosapentaenoyl)-O-phospho-L-tyrosine (16)

This compound was prepared as described above for (8), using 0.5 mmol (151 mg) of cis-5,8,11,14,17-eicosapentaenoic acid; yield 65 mg, (24%); $R_f$ 0.05–0.10 (system B); $^1$H-NMR (CD$_3$SOCD$_3$, 200 MHz) $\delta$0.9–1.0 (t, 3H, $\omega$-CH$_3$); 1.5–1.6 (t, 2H, CH$_2$); 2.0–2.2 (m, 6H, CH$_2$CO and 2CH$_2$CH=CH); 2.7–3.0 (m, 10H, 4HC=CH—CH$_2$—CH=CH and CH$_2$Ar); 4.3–4.4 (m, 1H, NHCHCO); 5.2–5.4 (br s, 10H, 5HC=CH); 7.1 (s, 4H, Ar); 8.2–8.4 (m, 3H, NH and 2POH)

Example 21
Synthesis of the N-(cis-9,12,15-octadecatrienoyl)-O-phospho-2-aminoethanol (N-linolenoyl-O-phospho-2-aminoethanol) (17)

This compound was prepared as described above for (5), using 0.5 mmol (139 mg) of cis-9,12,15-octadecatrienoic acid; yield 80 mg, (40%); $R_f$ 0.10–0.15 (system B); $^1$H-NMR (CD$_3$SOCD$_3$, 200 MHz) $\delta$0.9–1.0 (t, 8H, $\omega$-CH$_3$); 1.3(s, 8H, 4CH$_2$); 1.4–1.5(br, s, 2H, CH$_2$CH$_2$CO); 2.0–2.2 (m, 6H, CH$_2$CO and 2CH$_2$CH=CH); 2.7–2.9 (br s, 4H, 2HC=CH—CH$_2$—CH=CH); 3.1–3.2 (br s, 2H, CH$_2$NH); 3.7–3.8 (br s, 2H, CH$_2$OP); 5.2–5.4 (br s, 6H, 3HC=CH); 8.2–8.4 (m, 3H, NH and 2POH).

Example 22
Synthesis of the N-(cis-9,12,15-octadecatrienoyl)-O-phospho-L-serine (N-linolenoyl-O-phospho-L-serine) (18)

This compound was prepared as described above for (6), using 0.5 mmol (139 mg) of cis-9,12,15-octadecatrienoic acid; yield 73 mg (33%); $R_f$ 0.05–0.10 (system B); $^1$H-NMR (CD$_3$SOCD$_3$, 200 MHz) $\delta$0.9–1.0 (t, 3H, $\omega$-CH$_3$); 1.3 (s, 8H, 4CH$_2$); 1.4–1.5 (br s, 2H, CH$_2$CH$_2$CO); 2.0–2.2 (m, 6H, CH$_2$CO and 2 CH$_2$CH=CH); 2.7–2.9 (br s, 4H, 2HC=CH—CH$_2$—CH=CH); 3.9–4.0 (br s, 2H, CH$_2$OP); 4.3–4.4 (m, 1H, NH CHCO); 5.2–5.4 (br s, 6H, 3 HC=CH); 8.2–8.4 (m, 3H, NH and 2POH).

Example 23
Synthesis of the N-(cis-9,12,15-octadecatrienoyl)-O-phospho-L-threonine (N-linolenoyl-O-phospho-L-threonine) (19)

This compound was prepared as described above for (6), using 0.5 mmol (139 mg) of cis-9,12,15-octadecatrienoic acid and 1 mmol (1 70 mg) of L-threonine methyl ester hydrochloride; yield 85 mg (37%); $R_f$ 0.05–0.10 (system B); $^1$H-NMR (CD$_3$SOCD$_3$, 200 MHz) $\delta$0.9–1.0 (t, 3H, $\omega$-CH$_3$); 1.3–1.5 (m, 13H, 5CH$_2$ and CH$_3$CHOP); 2.0–2.2 (m, 6H, CH$_2$CO and 2CH$_2$CH=CH); 2.7–2.9 (br s, 4H, 2HC=CH—CH$_2$—CH=CH); 4.1–4.3 (m, 2H, 2CH); 5.2–5.4 (br s, 6H, 3HC=CH); 8.2–8.4 (m, 3H, NH and 2POH)

Example 24

Synthesis of the N-(cis-9,12,15-octadecatrienoyl)-O-phospho-L-tyrosine (N-linolenoyl-O-phospho-L-tyrosine) (20)

This compound was prepared as described above for (8), using 0.5 mmol (139 mg) of cis-9,12,15-octadecatrienoic acid; yield 52 mg (20%); $R_f$ 0.05–0.10 (system B); $^1$H-NMR (CD$_3$SOCD$_3$, 200 MHz) δ0.9–1.0 (t, 3H, ω-CH$_3$); 1.3(s, 8H, 4CH$_2$); 1.4–1.5 (br, s, 2H, CH$_2$CH$_2$CO); 2.0–2.2 (m, 6H, CH$_2$CO and 2CH$_2$CH=CH); 2.7–2.9 (br s, 4H, 2HC=CH—CH$_2$—CH=CH );2.9–3.1(m, 2H, CH$_2$Ar); 4.3–4.4 (m, 1H, NHCHCO); 5.2–5.4 (br s, 6H, 3HC=CH); 7,0 (s, 4H, Ar); 8.2–8.4 (m, 3H, NH and 2POH).

Example 25

The Influence of Compound 10 on Humoral Immune Response 0.15 ml of compound 10 was administered intravenously to 6 mice females of CS7B1/6 line (weight 18–22 g) in doses of 45.5, 91 and 136.5 μg of compound 10 per capita for each testing group according to the dose. Simultaneously, a suspension of 5·10$^7$ sheep erythrocytes was injected intraperitoneally (0.2 ml per capita). Mice in the control group were injected intravenously with equal volume of saline. The effects of compound 10 on humoral immune response were analyzed both by counting the quantity of AFC in the spleen according to Cunningham (per 10$^6$ spleen cells and per spleen) and estimating the titers of hemagglutining antibodies in serum of the animals (Cunningham A. J., Nature, 1965, Vol.207, No 5001. P.1106–1107), while the titers of hemagglutinating antibodies were evaluated according to litterature (Evans J. et al., Cell, 1974; Vol 3., p.153–158, Feizi T., Menger E., Transfusion, 1970, Vol. 10, p.33–35,).

The relative amount of AFC on the 5-th day after injection was 273.3±20.4 for control animals, 304.9±46.6 for the experimental group with compound 10 in the dose of 45.5 μg/mouse, p>0.05, 326.2±65.4 for the group with compound 10 in the dose of 91 μg/mouse, p>0.05, and 651.6±48.2 for the experimental group with compound 10 in the dose of 136.5 μg/mouse, p<0.001. The total AFC amount was $(31.3±2.5) \cdot 10^3$ for the control group, $(30.2±5.7) \cdot 10^3$ for the experimental group receiving compound 10 in the dose of 45.5 μg/mouse, p>0.05, $(34.7±8.5) \cdot 10^3$ for the group receiving compound 10 in the dose of 91 μg/mouse, p>0.05, and $(81.1±5.8) \cdot 10^3$ for the experimental group receiving compound 10 in the dose of 136.5 μg/mouse, p<0.001. Moreover, compound 10 in the dose of 136.5 μg/mouse caused significant increase of hemagglutinin titres in serum of immunised mice, those were 7.0±0.4 for control animals and 8.5±0.4 for the group receiving compound 10 in the dose of 136.5 μg/mouse, p<0.05 (Table 1).

The immunogenic activity of compound 10 is dose-dependent. Compound 10 in the doses of 45.5 and 91 μg/mouse exhibits no immunogenic activity, but at the same time compound 13 in the dose of 136.5 μg/mouse displayed high immunostimulating action. Thus, the relative amount of AFC on the 5-th day after injection of the compound 10 increased by 138%, and total AFC amount increased by 159% in comparison to the amount of cells in animals immunized only with sheep erythrocytes, when hemagglutinin titres in serum of immunised mice increased by 21%.

Example 26

The Influence of Compound 11 on Humoral Immune Response 0.15 ml of compound 11 was administered intravenously to 6 female mice of the C57B1/6 line (weight 18–22 g) in doses of 45.5, 91 and 136.5 μg of compound 11 per capita for each testing group according to the dose. Simultaneously, a suspension of 5·10$^7$ sheep erytrocytes was injected intraperitoneally (0.2 ml per capita). Mice in the control group were injected intravenously with an equal volume of saline. The effects of compound 11 on humoral immune response was analysed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 799.3±63.3 for control animals, 676.8±77.1 for the experimental group receiving compound 11 in the dose of 45.5 μg/mouse, p>0.05, 896.8±111.8 for the group receiving compound 11 in the dose of 91 μg/mouse, p>0.05, and 1336.5±59.0 for the experimental group receiving compound 11 in the dose of 136.5 μg/mouse, p<0.001. The total AFC amount was $(101.1±8.6) \cdot 10^3$ for the controls, $(85.9±8.3) \cdot 10^3$ for the experimental group receiving compound 11 in the dose of 45.5 μg/mouse, p>0.05, $(111.2±11.8) \cdot 10^3$ for the group receiving compound 11 in the dose of 91 μg/mouse, p>0.05, and $(182.5±7.8) \cdot 10^3$ for the experimental group receiving compound 11 in the dose of 136.5 μg/mouse, p<0.001. Moreover, compound 11 in the dose of 136.5 μg/mouse caused significant increase of hemagglutinin titers in serum of immunized mice, those were 8.3±0.3 for control animals and 9.3±0.2 for group with compound 11 in the dose of 136.5 μg/mouse, p<0.02 (Table 2).

The immunogenic activity of compound 11 is dose-dependent. Compound 11 in the doses of 45.5 and 91 μg/mouse exhibits no immunogenic activity, but at the same time in the dose of 136.5 μg/mouse the same compound 11 displayed marked immunostimulating action. Thus, the relative amount of AFC on the 5-th day after injection of the compound 11 increased by 67%, and the total AFC amount increased by 80% in comparison with amount of cells in the animals immunized only with sheep erythrocytes, when the hemagglutinin titers in serum of immunized mice increased by 12%.

Example 27

The Influence of Compound 12 on Humoral Immune Response 0.15 ml of compound 12 was administered intravenously to 6 female mice of the C57B1/6 line (weight 18–22 g) in doses of 45.5, 91 and 136.5 μg of compound 12 per capita for each testing group according to the dose. Simultaneously, a suspension of 5·10$^7$ sheep erythrocytes was injected intraperitoneally (0.2 ml per capita). Mice in the control group were injected intravenously with an equal volume of saline. The effects of compound 12 on humoral immune response was analyzed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 291.1±14.3 for the control animals, 263.8±23.6 for the experimental group receiving compound 12 in the dose of 45.5 μg/mouse, p>0.05, 307.8±30.9 for the group receiving compound 12 in the dose of 91 μg/mouse, p>0.05, and 682.6±33.3 for the experimental group receiving compound 12 in the dose of 136.5 μg/mouse, p<0.001. The total AFC amount was $(35.0±3.3) \cdot 10$ for the controls, $(31.8±2.8) \cdot 10^3$ for the experimental group receiving compound 12 in the dose of 45.5 μg/mouse, p>0.05, $(40.2±2.7) \cdot 10^3$ for the group receiving compound 12 in the dose of 91 μg/mouse, p>0.05, and $(69.6±6.0) \cdot 10^3$ for the experimental group receiving compound 12 in the dose of 136.5 μg/mouse, p<0.001(Table 3).

The immunogenic activity of compound 12 is dose-dependent. Compound 12 in the doses of 45.5 and 91 μg/mouse exhibits no immunogenic activity, but at the same time in the dose of 136.5 µg/mouse the same compound 12 displayed high immunostimulating action. Thus, the relative amount of AFC on the 5-th day after injection of the compound 12 increased by 134%, and total AFC amount increased 99% in comparison with amount of cells in the animals immunized only with sheep erythrocytes.

Example 28

The Influence of Compound 8 on Humoral Immune Response 0.15 ml of compound 8 was administered intravenously to 6 female mice of the C57B1/6 line (weight 18–22 g) in doses of 45.5, 91 and 136.5 µg of compound 8 per capita for each testing group according to the dose. Simultaneously, a suspension of $5 \cdot 10^7$ sheep erythrocytes was injected intraperitoneally (0.2 ml per capita). Mice of the control group were injected intravenously with an equal volume of saline. The effects of compound 8 on humoral immune response were analyzed both by counting the quantity of AFC in the spleen according to Cunningham (per $10^6$ spleen cells and per spleen) and estimating the titers of hemagglutining antibodies in serum of the animals.

The relative amount of AFC on the 5-th day after injection was 501.7±21.0 for the control animals, 449.1±37.4 for the experimental group receiving compound 8 in the dose of 45.5 µg/mouse, p>0.05, 592.2±41.6 for the group receiving compound 8 in the dose of 91 µg/mouse, p>0.05, and 657.8±24.0 for the experimental group receiving compound 8 in the dose of 136.5 µg/mouse, p<0.001. The total AFC amount was $(46.5±2.4) \cdot 10^3$ for control group, $(44.4±4.3) \cdot 10^3$ for the experimental group receiving compound 8 in the dose of 45.5 µg/mouse, p>0.05, $(50.9±4.5) \cdot 10^3$ for the group receiving compound 8 in the dose of 91 µg/mouse, p>0.05, and $(88.8±8.0) \cdot 10^3$ for the experimental group receiving compound 8 in the dose of 136.5 µg/mouse, p<0.001 (Table 4).

The immunogenic activity of compound 8 is dose-dependent. Compound 8 in the doses of 45.5 and 91 µg/mouse exhibits no immunogenic activity, but at the same time in the dose of 136.5 µg/mouse the compound 8 displayed marked immunostimulating action. Thus, the relative amount of AFC on the 5-th day after injection of the compound 8 increased by 31%, and total AFC amount increased by 91% in comparison with the amount of cells in the animals immunised only with sheep erythrocytes.

Example 29

The Influence of Compound 3 on Humoral Immune Response 0.15 ml of compound 3 was administered intravenously to 6 female mice of the C57B1/6 line (weight 18–22 g) in doses of 45.5, 91 and 136.5 µg of compound 3 per capita for each testing group according to the dose. Simultaneously, a suspension of $5 \cdot 10^7$ sheep erytrocytes was injected intraperitoneally (0.2 ml per capita). Mice of the control group were injected intravenously with equal volume of saline. The effects of compound 3 on humoral immune response were analysed both by counting the quantity of AFC in the spleen according to Cunningham (per $10^6$ spleen cells and per spleen) and estimating the titers of hemagglutining antibodies in serum of the animals.

The relative amount of AFC on the 5-th day after injection was 407.4±10.7 for control animals; 472.2±52.4 for the experimental group receiving compound 3 in the dose of 45.5 µg/mouse, p>0.05; 827.7±34.6 for the group receiving compound 3 in the dose of 91 µg/mouse, p<0.001, and 961.3±56.5 for the experimental group receiving compound 3 in the dose of 136.5 µg/mouse, p<0.001. The total AFC amount was $(40.5±2.9) \cdot 10^3$ for the control group; $(44.6±3.9) \cdot 10^3$ for the experimental group receiving compound 3 in the dose of 45.5 µg/mouse, p>0.05, $(60.3±4.1) \cdot 10^3$ for the group receiving compound 3 in the dose of 91 µg/mouse, p<0.01, and $(107.0±8.5) \cdot 10^3$ for the experimental group receiving compound 3 in the dose of 136.5 µg/mouse, p<0.001. Moreover, compound 3 in doses of 91 and 136.5 µg/mouse caused significant increase of the hemagglutinin titers in serum of immunised mice, those were 6.3±0.3 for control animals, 8.0±0.3 for the group receiving compound 3 in the dose of 91 µg/mouse, p<0.01, and 8.7±0.3 for the group receiving compound 3 in the dose of 136.5 µg/mouse, p<0.001 (Table 5).

The immunogenic activity of compound 3 is dose-dependent. Compound 3 in the dose of 45.5 µg/mouse exhibits no immunogenic activity, but at the same time in doses of 91 and 136.5 µg/mouse compound 3 displayed high immunostimulating action. Thus, the relative amount of AFC on the 5-th day after injection of the compound 3 increased by 103 and 136%, and total AFC amount increased by 49% and 164% accordingly in comparison with the amount of cells in the animals immunized only with sheep erythrocytes, when the hemagglutinin titer in serum of immunized mice increased by 27% and 38%.

Example 30

The Influence of Compound 4 on Humoral Immune Response 0.15 ml of compound 4 was administered intravenously to 6 female mice of the C57B1/6 line (weight 18–22 g) in a doses of 45.5, 91 and 136.5 µg of compound 4 per capita for each testing group according to the dose. Simultaneously, a suspension of $5 \cdot 10^7$ sheep erythrocytes was injected intraperitoneally (0.2 ml per capita). Mice of the control group were injected intravenously with an equal volume of saline. The effects of compound 4 on humoral immune response were analyzed both by counting the quantity of AFC in the spleen according to Cunningham (per $10^6$ spleen cells and per spleen) and estimating the titers of hemagglutining antibodies in serum of the animals.

The relative amount of AFC on the 5-th day after injection was 406.4±16.8 for the control animals; 405.0±47.9 for the experimental group receiving compound 4 in a dose of 45.5 µg/mouse, p>0.05; 692.9±44.8 for the group receiving compound 4 in a dose of 91 µg/mouse, p<0.001, and 1354.3±99.9 for the experimental group receiving compound 4 in a dose of 136.5 µg/mouse, p<0.001. The total AFC amount was $(60.4±3.9) \cdot 10^3$ for the control group, $(55.0±6.7) \cdot 10^3$ for the experimental group receiving compound 4 in a dose of 45.5 µg/mouse, p>0.05, $(87.6±4.3) \cdot 10^3$ for the group receiving compound 4 in a dose of 91 µg/mouse, p<0.001, and $(138.9±10.0) \cdot 10^3$ for the experimental group receiving compound 4 in a dose of 136.5 µg/mouse, p<0.001. Moreover, compound 4 in the dose of 136.5 µg/mouse caused significant increase of titers of hemagglutinins in serum of immunized mice, those were 6.2±0.3 for control animals and 7.5±0.2 for the group receiving compound 4 in the dose of 136.5 µg/mouse, p<0.01 (Table 6).

The immunogenic activity of compound 4 is dose-dependent. Compound 4 in the dose of 45.5 µg/mouse exhibits no immunogenic activity, but at the same time in doses of 91 and 136.5 µg/mouse the compound 4 displayed high immunostimulating action. Thus, the relative amount of AFC on the 5-th day after injection of the compound 4 increased by 70% and 233%, and total AFC amount increased by 45% and 130% accordingly in comparison with amount of cells in the animals immunized only with sheep erythrocytes, when a titers of hemagglutinins in serum of immunized mice raised of 21%.

TABLE 1

Effect of compound 10, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins Log$_2$ T | Effect, % and p |
|---|---|---|---|---|---|---|---|---|
| None | 5.9 ± 0.5 | — | 273.3 ± 20.4 | — | 31.3 ± 2.5 | — | 7.0 ± 0.4 | — |
| 45.5 | 6.9 ± 0.2 | p > 0.05 | 304.9 ± 46.6 | +11.6 p > 0.05 | 30.2 ± 5.7 | −3.5 p > 0.05 | 7.8 ± 0.3 | +11.4 p > 005 |
| 91.0 | 6.6 ± 0.4 | p > 0.05 | 326.2 ± 65.4 | +19.4 p > 0.05 | 34.7 ± 8.5 | +10.9 p > 0.05 | 7.8 ± 0.3 | +11.4 p > 005 |
| 136.5 | 6.7 ± 0.2 | p > 0.05 | 651.6 ± 48.2 | +138.4 p < 0.001 | 81.1 ± 5.8 | +159.1 p < 0.001 | 8.5 ± 0.4 | +21.4 p < 0.05 |

TABLE 2

Effect of compound 11, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins Log$_2$ T | Effect, % and p |
|---|---|---|---|---|---|---|---|---|
| None | 6.5 ± 0.6 | — | 799.3 ± 63.3 | — | 101.1 ± 8.6 | — | 8.3 ± 0.3 | — |
| 45.5 | 6.2 ± 0.2 | p > 0.05 | 676.8 ± 77.1 | −15.3 p > 0.05 | 85.9 ± 8.3 | −15.0 p > 0.05 | 8.3 ± 0.3 | 0 |
| 91.0 | 6.9 ± 0.5 | p > 0.05 | 896.8 ± 111.8 | +12.2 p > 0.05 | 111.2 ± 11.8 | +10.0 p > 0.05 | 8.0 ± 0.5 | −3.6 p > 0.05 |
| 136.5 | 7.5 ± 0.4 | p > 0.05 | 1336.5 ± 59.0 | +67.2 p < 0.001 | 182.5 ± 7.8 | +80.5 p < 0.001 | 9.3 ± 0.2 | +12.0 p < 0.02 |

TABLE 3

Effect of compound 12, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins Log$_2$ T | Effect, % and p |
|---|---|---|---|---|---|---|---|---|
| None | 6.2 ± 0.5 | — | 291.1 ± 14.3 | — | 35.0 ± 3.3 | — | 7.2 ± 0.3 | — |
| 45.5 | 6.3 ± 0.3 | p > 0.05 | 263.8 ± 23.6 | −9.4 p >0.05 | 31.8 ± 2.8 | −9.1 p >0.05 | 7.4 ± 0.3 | +2.8 p >0.05 |
| 91.0 | 5.9 ± 0.3 | p > 0.05 | 307.8 ± 30.9 | +5.7 p > 0.05 | 40.2 ± 2.7 | +14.9 p > 0.05 | 7.4 ± 0.3 | +2.8 p > 0.05 |
| 136.5 | 6.3 ± 0.4 | p > 0.05 | 682.6 ± 33.3 | +134.5 p < 0.001 | 69.6 ± 6.0 | +98.9 p < 0.001 | 7.8 ± 0.3 | +7.7 p > 0.05 |

TABLE 4

Effect of compound 8, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins Log$_2$ T | Effect, % and p |
|---|---|---|---|---|---|---|---|---|
| None | 5.2 ± 0.2 | — | 501.7 ± 21.0 | — | 46.5 ± 2.4 | — | 8.5 ± 0.2 | — |
| 45.5 | 5.2 ± 0.1 | — | 449.1 ± 37.4 | −10.5 p > 0.05 | 44.4 ± 4.3 | −4.5 p > 0.05 | 8.3 ± 0.3 | −2.4 p > 0.05 |
| 91.0 | 5.1 ± 0.3 | p > 0.05 | 592.2 ± 41.6 | +18.0 p > 0.05 | 50.9 ± 4.5 | +9.5 p > 0.05 | 8.8 ± 0.3 | +3.5 p > 0.05 |
| 136.5 | 5.3 ± 0.3 | p > 0.0S | 657.8 ± 24.0 | +31.1 p < 0.001 | 88.8 ± 8.0 | +91.0 p < 0.001 | 8.5 ± 0.2 | 0 |

TABLE 5

Effect of compound 3, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins Log$_2$ T | Effect, % and p |
|---|---|---|---|---|---|---|---|---|
| None | 6.2 ± 0.3 | — | 407.4 ± 10.7 | — | 40.5 ± 2.9 | — | 6.3 ± 0.3 | — |
| 45.5 | 6.1 ± 0.3 | p > 0.05 | 472.2 ± 52.4 | +15.9 p > 00.05 | 44.6 ± 3.9 | +10.1 p > 0.05 | 6.6 ± 0.2 | +4.8 p > 0.05 |
| 91.0 | 6.2 ± 0.2 | p > 0.05 | 827.7 ± 34.6 | +103.2 p < 0.001 | 60.3 ± 4.1 | +48.9 p < 0.01 | 8.0 ± 0.3 | +27.0 p < 0.01 |
| 136.5 | 6.8 ± 0.3 | p > 0.05 | 961.3 ± 56.5 | +136.0 p < 0.001 | 107.0 ± 8.5 | +164.2 p < 0.001 | 8.7 ± 0.3 | +38.1 p < 0.001 |

TABLE 6

Effect of compound 4, injected intravenously simultaneously with the antigen (5 × 10$^7$ SRBC/mouse, intraperitoneally), on the humoral immune response in C57B1/6 female mice (n = 6)

| Treatment dose, μg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hemagglutinins, Log$_2$ T | Effect, % and p |
|---|---|---|---|---|---|---|---|---|
| None | 6.6 ± 0.3 | — | 406.4 ± 16.8 | — | 60.4 ± 3.9 | — | 6.2 ± 0.3 | — |
| 45.5 | 6.6 ± 0.5 | — | 405.0 ± 47.9 | −0.3 p >0.05 | 55.0 ± 6.7 | −8.9 p > 0.05 | 6.0 ± 0.3 | −3.2 p > 0.05 |
| 91.0 | 6.3 ± 0.4 | p > 0.05 | 692.9 ± 44.8 | +70.5 p < 0.001 | 87.6 ± 4.3 | +45.0 p < 0.001 | 6.5 ± 0.4 | +4.8 p > 0.05 |
| 136.5 | 6.0 ± 0.5 | p > 0.05 | 1354.3 ± 99.9 | +233.2 p < 0.001 | 138.9 ± 10.0 | +130.0 p < 0.001 | 7.5 ± 0.2 | +21.0 p < 0.01 |

Example 31

The Influence of Compound 13 on Humoral Immune Response 0.15 ml of compound 13 was administered intravenously to 6 female mice of the C57B1/6 line (weight 18–22 g) in doses of 45.5, 91 and 136.5 g of compound 13 per capita for each testing group according to the dose. Simultaneously, a suspension of 5·10$^7$ sheep erytrocytes was injected intraperitoneally (0.2 ml per capita). Mice of control group were injected intravenously with equal volume of saline. Compound 13 effects on humoral immune response were analyzed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 628.6±34.9 for the control animals, 608.2±61.3 for the experimental group receiving compound 13 in a dose of 45.5 μg/mouse, p>0.05, 525.0±97.2 for the group receiving compound 13 in a dose of 91 μg/mouse, p>0.05, and 885.9±65.8 for the experimental group receiving compound 13 in a dose of 136.5 μg/mouse, p<0.01. The total AFC amount was (45.9±5.2)·10$^3$ for control group, (48.2±6.5)·10$^3$ for the experimental group receiving compound 13 in a dose of 45.5 μg/mouse, p>0.05, (49.4±6.2)·10$^3$ for the group receiving compound 13 in a dose of 91 μg/mouse, p>0.05, and (68.2±6.9)·10$^3$ for the experimental group receiving compound 13 in the dose of 136.5 μg/mouse, p<0.05 (Table 7).

The immunogenic activity of compound 13 is dose-dependent. Compound 13 in doses of 45.5 and 91 μg/mouse exhibit no immunogenic activity, but at the same time in the dose of 136.5 μg/mouse the compound 13 displayed marked immunostimulating action. Thus, the relative amount of AFC on the 5-th day after injection of the compound 13 increased by 41%, and total AFC amount increased by 49% in comparison with amount of cells in the animals immunized only with sheep erythrocytes.

Example 32

Compound 1a Influence on Humoral Immune Response 0.15 ml of compound 1a was administered intravenously to 6 female mice of C57B1/6 line (weight 18–22 g) in a doses of 45.5, 91 and 136.5 μg of compound 1a per capita for each testing group according to the dose. Simultaneously, a suspension of 5·10$^7$ sheep erythrocytes was injected intraperitoneally (0.2 ml per capita). Mice of control group were injected intravenously with equal volume of saline. Compound 1a effects on humoral immune response were analyzed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 772.3±47.8 for control animals, 815.8±70.9 for the experimental group receiving compound 1a in the dose of 45.5 μg/mouse, p>0.05, 997.2±43.4 for the group receiving compound 1a in the dose of 91 μg/mouse, p<0.01, and 1176.9±58.5 for the experimental group receiving compound 1a in the dose of 136.5 μg/mouse, p<0.001. The total AFC amount was (89.9±5.9)·10$^3$ for control group, (104.6±10.7)·10$^3$ for the experimental group receiving compound 1a in the dose of 45.5 μg/mouse, p>0.05, (114.5±8.2)·10$^3$ for the group receiving compound 1a in the dose of 91 μg/mouse, p<0.05, and (149.4±9.4)·10$^3$ for the experimental group receiving compound 1a in the dose of 136.5 μg/mouse, p<0.001 (Table 8).

Immunogenic activity of compound 1a is dose-dependent. Compound 1a in the dose of 45.5 μg/mouse exhibits no immunogenic activity, but at the same time in doses of 91 and 136.5 μg/mouse the compound 1a displayed marked immunostimulating action. Thus, the relative amount of AFC on the 5-th day after injection of the compound 1a increased by 29% and 52%, and total AFC amount increased by 27% and 66% correspondingly in comparison with amount of cells in the animals immunized only with sheep eyrocytes.

Example 33
Compound 14 Influence on Humoral Immune Response 0.15 ml of compound 14 was administered intravenously to 6 mice females of C57B1/6 line (weight 18–22 g) in a doses of 45.5, 91 and 136.5 µg of compound 13 per capita for each testing group according to the dose. Simultaneously suspension of 5·10⁷ sheep erythrocytes was injected intraperitoneally (0.2 ml per capita). Mice of control group were injected intravenously with equal volume of saline. Compound 14 effects on humoral immune response were analyzed both by counting the quantity of AFC in the spleen according to Cunningham (per 10⁶ spleen cells and per spleen) and estimating the titers of hemagglutining antibodies in serum of the animals.

The relative amount of AFC on the 5-th day after injection was 622.3±19.1 for the control animals, 554.6±52.0 for the experimental group receiving compound 14 in a dose of 45.5 µg/mouse, $p>0.05$, 645.8±64.4 for the group receiving compound 14 in a dose of 91 µg/mouse, $p>0.05$, and 946.1±41.9 for the experimental group receiving compound 14 in a dose of 136.5 µg/mouse, $p<0.001$. The total AFC amount was $(71.9±12.0)·10^3$ for the control group, $(70.8±10.8)·10^3$ for the experimental group receiving compound 14 in a dose of 45.5 µg/mouse, $p>0.05$, $(80.8±12.7)·10^3$ for the group receiving compound 14 in a dose of 91 µg/mouse, $p>0.05$, and $(108.6±10.8)·10^3$ for the experimental group receiving compound 14 in the dose of 136.5 µg/mouse, $p<0.05$ (Table 9).

The immunogenic activity of compound 14 is dose-dependent. Compound 14 in doses of 45.5 and 91 µg/mouse exhibits no immunogenic activity, but at the same time in the dose of 136.5 µg/mouse the compound 14 displayed marked immunostimulating action. Thus, the relative amount of AFC on the 5-th day after injection of the compound 14 increased by 52%, and total AFC amount increased by 51% in comparison with amount of cells in the animals immunized only with sheep erythrocytes.

Example 34
Compound 2a Influence on Humoral Immune Response 0.15 ml of compound 2a was administered intravenously to 6 mice females of C57B1/6 line (weight 18–22 g) in a doses of 45.5, 91 and 136.5 µg of compound 2a per capita for each testing group according to the dose. Simultaneously, a suspension of 5·10⁷ sheep erythrocytes was injected intraperitoneally (0.2 ml per capita). Mice in the control group were injected intravenously with an equal volume of saline. The effects of compound 2a on humoral immune response were analyzed both by counting the quantity of AFC in the spleen according to Cunningham (per 10⁶ spleen cells and per spleen) and estimating the titers of hemagglutining antibodies in serum of the animals.

The relative amount of AFC on the 5-th day after injection was 303.3±14.4 for the control animals, 264.5±19.9 for the experimental group receiving compound 2a in a dose of 45.5 µg/mouse, $p>0.05$, 585.6±51.6 for the group receiving compound 2a in a dose of 91 µg/mouse, $p<0.001$, and 639.8±54.6 for the experimental group receiving compound 2a in dose of 136.5 µg/mouse, $p<0.001$. The total AFC amount was $(40.0±3.7)·10^3$ for the control group, $(34.0±2.6)·10^3$ for the experimental group receiving compound 2a in a dose of 45.5 µg/mouse, $p>0.05$, $(59.4±5.2)·10^3$ for the group receiving compound 2a in a dose of 91·µg/mouse, $p<0.02$, and $(68.3±6.1)·10^3$ for the experimental group receiving compound 2a in a dose of 136.5 µg/mouse, $p<0.01$ (Table 10).

The immunogenic activity of compound 2a is dose-dependent. Compound 2a in the dose of 45.5 µg/mouse exhibit no immunogenic activity, but at the same time in doses of 91 and 136.5 µg/mouse the compound 2a displayed marked immunostimulating action. Thus, the relative amount of AFC on the 5-th day after injection of the compound 2a increased by 93% and 111%, and total AFC amount increased by 48% and 71% correspondingly in comparison with amount of cells in the animals immunized only with sheep erythrocytes.

TABLE 7

Effect of compound 13, injected intravenously simultaneously with the antigen (5 × 10⁷ SRBC/mouse, intraperitoneally), on the humoral immune response in C57B1/6 female mice (n = 6)

| Treatment dose, µg | Spleen index, 10⁻³ | p | Amount of antibody-forming cells per 10⁶ spleen cells, M ± SEM | Effect, % and p | Amount of antibody-forming cells per spleen, × 10³, M ± SEM | Effect, % and p | Amount of hema-gglutinins, Log₂ T | Effect, % and p |
|---|---|---|---|---|---|---|---|---|
| None | 5.6 ± 0.6 | — | 628.6 ± 34.9 | — | 45.9 ± 5.2 | — | 9.0 ± 0.5 | — |
| 45.5 | 5.4 ± 0.6 | p > 0.05 | 608.2 ± 61.3 | −3.2 p > 0.05 | 48.2 ± 6.5 | +5.0 p > 0.05 | 9.7 ± 1.2 | +7,8 p > 0.05 |
| 91.0 | 5.7 ± 0.8 | p > 0.05 | 525.0 ± 97.2 | −16.5 p > 0.05 | 49.4 ± 6.2 | +7.6 p > 0.65 | 9.5 ± 1.2 | +5,6 p > 0.05 |
| 136.5 | 5.3 ± 0.4 | p > 0.05 | 885.9 ± 65.8 | +40.9 p < 0.01 | 68.2 ± 6.9 | +48.6 p < 0.05 | 10.3 ± 0.9 | +14,4 p > 0.05 |

TABLE 8

Effect of compound 1a, injected intravenously simultaneously with the antigen (5 × 10⁷ SRBC/mouse, intraperitoneally), on the humoral immune response in C57B1/6 mice female (n = 6)

| Treatment dose, µg | Spleen index, 10⁻³ | p | Amount of antibody-forming cells per 10⁶ spleen cells, M ± SEM | Effect, % and p | Amount of antibody-forming cells per spleen, × 10³, M ± SEM | Effect, % and p | Amount of hema-gglutinins, Log₂ T | Effect, % and p |
|---|---|---|---|---|---|---|---|---|
| None | 6.2 ± 0.4 | — | 772.3 ± 47.8 | — | 89.9 ± 5.9 | — | 7.7 ± 0.2 | — |
| 45.5 | 6.1 ± 0.2 | p > 0.05 | 815.8 ± 70.9 | +5.6 p > 0.05 | 104.6 ± 10.7 | +16.4 p > 0.05 | 7.6 ± 0.3 | −1,3 p > 0.05 |
| 91.0 | 6.2 ± 0.2 | — | 997.2 ± 43.4 | +29.1 p < 0.01 | 114.5 ± 8.2 | +27.4 p < 0.05 | 7.6 ± 0.2 | −1,3 p > 0.05 |
| 136.5 | 6.9 ± 0.3 | p > 0.05 | 1176.9 ± 58.5 | +52.4 p < 0.001 | 149.4 ± 9.4 | +66.2 p < 0.001 | 8.2 ± 0.4 | +6,5 p > 0.05 |

TABLE 9

Effect of compound 14, injected intravenously simultaneously with the antigen (5 × 10$^7$ SRBC/mouse, intraperitoneally), on the humoral immune response in C57B1/6 female mice (n = 6)

| Treatment dose, µg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hema-gglutinins, Log$_2$ T | Effect, % and p |
|---|---|---|---|---|---|---|---|---|
| None | 6.6 ± 0.3 | — | 622.3 ± 19.1 | — | 71.9 ± 12.0 | — | 7.2 ± 0.2 | — |
| 45.5 | 6.5 ± 0.2 | p > 0.05 | 554.6 ± 52.0 | −10.9 p > 0.05 | 70.8 ± 10.8 | −1.5 p > 0.05 | 6.5 ± 0.3 | −9,7 p > 0.05 |
| 91.0 | 6.2 ± 0.2 | p > 0.05 | 645.8 ± 64.4 | +3.8 p > 0.05 | 80.8 ± 12.7 | +12.4 p > 0.05 | 7.0 ± 0.3 | −2,8 p > 0.05 |
| 136.5 | 6.5 ± 0.3 | p > 0.05 | 946.1 ± 41.9 | +52.0 p < 0.001 | 108.6 ± 10.8 | +51.0 p < 0.05 | 7.2 ± 0.2 | 0 |

TABLE 10

Effect of compound 2a, injected intravenously simultaneously with the antigen (5 × 10$^7$ SRBC/mouse, intraperitoneally), on the humoral immune response in C57B1/6 female mice (n = 6)

| Treatment dose, µg | Spleen index, 10$^{-3}$ | p | Amount of antibody-forming cells per 10$^6$ spleen cells, M ± SEM | Effect, % and p | Amount of antibody-forming cells per spleen, × 10$^3$, M ± SEM | Effect, % and p | Amount of hema-gglutinins, Log$_2$ T | Effect, % and p |
|---|---|---|---|---|---|---|---|---|
| None | 7.3 ± 0.4 | — | 303.3 ± 14.4 | — | 40.0 ± 3.7 | — | 7.8 ± 0.4 | — |
| 45.5 | 6.4 ± 0.2 | p > 0.05 | 264.5 ± 19.9 | −12.8 p > 0.05 | 34.0 ± 2.6 | −15.0 p > 0.05 | 7.2 ± 0.3 | −7.7 p > 0.05 |
| 91.0 | 6.5 ± 0.2 | p > 0.05 | 585.6 ± 51.6 | +93.1 p < 0.001 | 59.4 ± 5.2 | +48.5 p < 0.02 | 7.5 ± 0.2 | −3.8 p > 0.05 |
| 136.5 | 7.4 ± 0.4 | p > 0.05 | 639.8 ± 54.6 | +110.9 p < 0.001 | 68.3 ± 6.1 | +70.8 p < 0.01 | 8.2 ± 0.4 | +5.1 p > 0.05 |

Example 35

The Influence of Compound 17 on Humoral Immune Response 0.15 ml of compound 17 was administered intravenously to 6 female mice of C57B1/6 line (weight 18–22 g) in doses of 45.5, 91 and 136.5 µg of compound 17 per capita for each testing group according to the dose. Simultaneously, a suspension of 5·10$^7$ sheep erytrocytes was injected intraperitoneally (0.2 ml per capita). A mice of control group were injected intravenously with an equal volume of saline. The effects of compound 17 on humoral immune response were analyzed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 471.5±44.6 for control animals, 457.3±40.7 for experimental group with compound 17 in the dose of 45.5 µg/mouse, p>0.05, 523.8±45.3 for group with compound 17 in the dose of 91 µg/mouse, p>0.05, and 619.6±38.9 for experimental group with compound 17 in the dose of 136.5 µg/mouse, p<0.05. The total AFC amount was (55.2±4.9)·10$^3$ for control group, (51.1±4.4)·10$^3$ for experimental group with compound 17 in the dose of 45.5 µg/mouse, p>0.05, (63.5±5.1)·10$^3$ for group with compound 17 in the dose of 91 µg/mouse, p>0.05, and (71.6±4.7)·10$^3$ for experimental group with compound 17 in the dose of 136.5 µg/mouse, p<0.05 (Table 11).

The immunogenic activity of compound 17 is dose-dependent. Compound 17 in the doses of 45.5 and 91 µg/mouse exhibit no immunogenic activity, but at the same time in the dose of 136.5 µg/mouse the compound 17 displayed marked immunostimulating action. Thus, the relative amount of AFC on the 5-th day after injection of the compound 17 increased of 31%, and total AFC amount increased of 30% in comparison with amount of cells in the animals immunized only with sheep erythrocytes.

Example 36

The Influence of Compound 19 on Humoral Immune Response 0.15 ml of compound 19 was administered intravenously to 6 mice females of C57B1/6 line (weight 18–22 g) in doses of 45.5, 91 and 136.5 µg of compound 19 per capita for each testing group according to the dose. Simultaneously, a suspension of 5·10$^7$ sheep erytrocytes was injected intraperitoneally (0.2 ml per capita). A mice of control group were injected intravenously with equal volume of saline. Compound 19 effects on humoral immune response were analyzed both by counting the quantity of AFC in the spleen according to Cunningham (per 10$^6$ spleen cells and per spleen) and estimating the titers of hemagglutining antibodies in serum of the animals.

The relative amount of AFC on the 5-th day after injection was 435.8±60.1 for control animals, 454.7±57.9 for experimental group with compound 19 in the dose of 45.5 µg/mouse, p>0.05, 473.2±44.5 for group with compound 19 in the dose of 91 µg/mouse, p>0.05, and 612.5±47.3 for experimental group with compound 19 in the dose of 136.5 µg/mouse, p<0.05. The total AFC amount was (46.3±5.7)·10$^3$ for control group, (48.8±6.4)·10$^3$ for experimental group with compound 19 in the dose of 45.5 µg/mouse, p>0.05, (51.2±6.1)·10$^3$ for group with compound 19 in the dose of 91 µg/mouse, p>0.05, and (64.7±4.9)·10$^3$ for experimental group with compound 19 in the dose of 136.5 µg/mouse, p<0.05 (Table 12).

Immnunogenic activity of compound 19 is dose-dependent. Compound 19 in the doses of 45.5 and 91 µg/mouse exhibit no immunogenic activity, but at the same time in the dose of 136.5 µg/mouse the compound 19 displayed marked immunostimulating action. Thus, the relative amount of AFC on the 5-th day after injection of the compound 19 increased of 41%, and total AFC amount increased of 40% in comparison with amount of cells in the animals immunized only with sheep erythrocytes.

Example 37
The Influence of Compound 20 on Humoral Immune Response 0.15 ml of compound 20 was administered intravenously to 6 female mice of C57B1/6 line (weight 18–22 g) in doses of 45.5, 91 and 136.5 µg of compound 20 per capita for each testing group according to the dose. Simultaneously, a suspension of $5 \cdot 10^7$ sheep erythrocytes was injected intraperitoneally (0.2 ml per capita). A mice of control group were injected intravenously with equal volume of saline. Compound 20 effects on humoral immune response were analyzed both by counting the quantity of AFC in the spleen according to Cunningham (per $10^6$ spleen cells and per spleen) and estimating the titers of hemagglutining antibodies in serum of the animals.

The relative amount of AFC on the 5-th day after injection was 568.3±34.6 for control animals, 512.8±46.2 for experimental group with compound 20 in the dose of 45.5 µg/mouse, p>0.05, 634.5±51.7 for group with compound 20 in the dose of 91 µg/mouse, p>0.05, and 845.1±43.1 for experimental group with compound 20 in the dose of 136.5 µg/mouse, p<0.001. The total AFC amount was $(50.1\pm3.2)\cdot 10^3$ for control group, $(46.4\pm4.8)\cdot 10^3$ for experimental group with compound 20 in the dose of 45.5 µg/mouse, p>0.05, $(55.7\pm5.6)\cdot 10^3$ for group with compound 20 in the dose of 91 µg/mouse, p>0.05, and $(75.8\pm7.7)\cdot 10^3$ for experimental group with compound 20 in the dose of 136.5 µg/mouse, p<0.02 (Table 13).

Immunogenic activity of compound 20 is dose-dependent. Compound 20 in the doses of 45.5 and 91 µg/mouse exhibit no immunogenic activity, but at the same time in the dose of 136.5 µg/mouse the compound 20 displayed marked immunostimulating action. Thus, the relative amount of AFC on the 5-th day after injection of the compound 20 increased of 49%, and total AFC amount increased of 51% in comparison with amount of cells in the animals immunized only with sheep erytrocytes.

TABLE 11

The effect of compound 17, injected intravenously simultaneously with the antigen ($5 \times 10^7$ SRBC/mouse, intraperitoneally), on the humoral immune response in C57B1/6 female mice (n = 6)

| Treatment dose, µg | Spleen index, $10^{-3}$ | p | Amount of antibody-forming cells per $10^6$ spleen cells, M ± SEM | Effect, % and p | Amount of antibody-forming cellsperspleen, $\times 10^3$, M ± SEM | Effect, % and p | Amount of hemagglutinins, $\text{Log}_2$ T | Effect, % and p |
|---|---|---|---|---|---|---|---|---|
| None | 5.8 ± 0.3 | — | 471.5 ± 44.6 | — | 55.2 ± 4.9 | — | 7.6 ± 0.3 | — |
| 45.5 | 5.8 ± 0.2 | — | 457.3 ± 40.7 | −3.0 p > 0.05 | 51.1 ± 4.4 | −7.4 p > 0.05 | 7.6 ± 0.2 | — |
| 91.0 | 5.7 ± 0.4 | p > 0.05 | 523.8 ± 45.3 | +11.1 p > 0.05 | 63.5 ± 5.1 | +15.0 p > 0.05 | 7.8 ± 0.3 | +2.6 p > 0.05 |
| 136.5 | 5.9 ± 0.3 | p > 0.05 | 619.6 ± 38.9 | +31.4 p < 0.05 | 71.6 ± 4.7 | +29.7 p < 0.05 | 7.8 ± 0.4 | +2.6 p > 0.05 |

TABLE 12

The effect of compound 19, injected intravenously simultaneously with the antigen ($5 \times 10^7$ SRBC/mouse, intraperitoneally), on the humoral immune response in C57B1/6 female mice (n = 6)

| Treatment dose, µg | Spleen index, $10^{-3}$ | p | Amount of antibody-forming cells per $10^6$ spleen cells, M ± SEM | Effect, % and p | Amount of antibody-forming cellsperspleen, $\times 10^3$, M ± SEM | Effect, % and p | Amount of hemagglutinins, $\text{Log}_2$ T | Effect, % and p |
|---|---|---|---|---|---|---|---|---|
| None | 6.2 ± 0.2 | — | 435.8 ± 60.1 | — | 46.3 ± 5.7 | — | 8.0 ± 0.3 | — |
| 45.5 | 6.2 ± 0.1 | — | 454.7 ± 57.9 | +4.3 p > 0.05 | 48.8 ± 6.4 | +5.4 p > 0.05 | 8.1 ± 0.3 | +1,3 p > 005 |
| 91.0 | 6.4 ± 0.2 | p > 0.05 | 473.2 ± 44.5 | +8.6 p > 0.05 | 51.2 ± 6.1 | +10.6 p > 0.05 | 8.3 ± 0.4 | +3.8 p > 0.05 |
| 136.5 | 6.5 ± 0.3 | p > 0.05 | 612.5 ± 47.3 | +40.5 p < 0.05 | 64.7 ± 4.9 | +39.7 p < 0.05 | 8.5 ± 0.3 | +6.3 p > 0.05 |

TABLE 13

The effect of compound 20, injected intravenously simultaneously with the antigen ($5 \times 10^7$ SRBC/mouse, intraperitoneally), on the humoral immune response in C57B1/6 female mice (n = 6)

| Treatment dose, µg | Spleen index, $10^{-3}$ | p | Amount of antibody-forming cells per $10^6$ spleen cells, M ± SEM | Effect, % and p | Amount of antibody-forming cells per spleen, $\times 10^3$, M ± SEM | Effect, % and p | Amount of hemagglutinins, $\text{Log}_2$ T | Effect, % and p |
|---|---|---|---|---|---|---|---|---|
| None | 6.2 ± 0.3 | — | 568.3 ± 34.6 | — | 50.1 ± 3.2 | — | 7.4 ± 0.3 | — |
| 45.5 | 6.3 ± 0.3 | p > 0.05 | 512.8 ± 46.2 | −9.8 p > 0.05 | 46.4 ± 4.8 | −7.4 p > 0.05 | 7.4 ± 0.2 | — |

TABLE 13-continued

The effect of compound 20, injected intravenously simultaneously with the antigen (5 × 10⁷ SRBC/mouse, intraperitoneally), on the humoral immune response in C57B1/6 female mice (n = 6)

| Treatment dose, µg | Spleen index, $10^{-3}$ | p | Amount of antibody-forming cells per $10^6$ spleen cells, M ± SEM | Effect, % and p | Amount of antibody-forming cells per spleen, × $10^3$, M ± SEM | Effect, % and p | Amount of hema-gglutinins, $Log_2$ T | Effect, % and p |
|---|---|---|---|---|---|---|---|---|
| 91.0 | 6.5 ± 0.2 | p > 0.05 | 634.5 ± 51.7 | +11.6 p > 0.05 | 55.7 ± 5.6 | +11.2 p > 0.05 | 7.5 ± 0.3 | +1.4 p > 0.05 |
| 136.5 | 6.4 ± 0.4 | p > 0.05 | 845.1 ± 43.1 | +48.7 p < 0.001 | 75.8 ± 7.7 | +51.3 p < 0.02 | 7.6 ± 0.4 | +2.7 p > 0.05 |

Example 38

The Influence of Human AFP/Compound 3 Complex (1:100) on Humoral Immune Response 0.15 ml of AFP/Compound 3 complex was administered intravenously to 6 mice males of C57B1/6 line (weight 18–22 g) in the dose of 9 g of AFP and 45.5 µg of compound 3 per capita. Simultaneously suspension of 5·10⁷ sheep erythrocytes was injected intraperitoneally (0.2 ml per capita). In the group with compound 3 mice were injected intravenously by one in the dose of 45.5 µg. Animals of group with AFP received 9 µg of AFP. Mice of control group were injected intravenously with equal volume of saline. Complex AFP/Compound 3 effect on humoral immune response was analyzed by counting the quantity of AFC in the spleen according to Cunningham (per $10^6$ spleen cells and per spleen).

The relative amount of AFC on the 5-th day after injection was 407.4±10.7 for control animals, 362.7±31.1 for experimental group with AFP, p>0.05, 472.2±52.4 for group with compound 3, p>0.05, and 716.4±49.2 for experimental group with AFP/Compound 3 complex, p<0.02. The total AFC amount was (40.5±2.9)·10³ for control group, (40.3±5.5)·10³ for experimental group with AFP, p>0.05, (44.6±3.9)·10³ for group with compound 3 alone, p>0.05, and (59.9±3.7)·10³ for experimental group with complex, p<0.05.

AFP and compound 3 alone exhibit no immunogenic activity. At the same time AFP/Compound 3 complex (1:100) displayed marked immunostimulating action. Thus, the relative amount of APC on the 5-th day after injection of the complex increased by 76%, and total AFC amount increased by 48% in comparison with amount of cells in the animals immunized only with sheep erythrocytes.

Example 39

The Influence of a Complex of Human AFP/Compound 2a (1:100) on Humoral Immune Response 0.15 ml of AFP/Compound 2a complex (1:100) was administered intravenously to 6 mice males of C57B1/6 line (weight 18–22 g) in the dose of 9 µg of AFP and 45.5 µg of compound 2a per capita. Simultaneously, a suspension of 5·10⁷ sheep erythrocytes was injected intraperitoneally (0.2 ml per capita). In the group with compound 2a mice were injected intravenously by one in the dose of 45.5 µg. Animals of group with AFP received 9 µg of AFP. Mice in the control group were injected intravenously with an equal volume of saline. The effect of the AFP/Compound 2a complex on humoral immune response was analyzed by counting the quantity of AFC in the spleen according to Cunningham (per $10^6$ spleen cells and per spleen).

The relative amount of AFC on the 5-th day after injection was 303.3±14.4 for the control animals, 334.5±32.8 for the experimental group receiving AFP, p>0.05, 264.5±19.9 for the group receiving compound 2a alone, p>0.05, and 537.8±32.4 for the experimental group receiving AFP/Compound 2a complex, p<0.05. The total AFC amount was (40.0±3.7)·10³ for the control group, (43.8±6.2)·10³ for the experimental group receiving AFP, p>0.05, (34.0±2.6)·10³ for the group receiving compound 2a alone, p>0.05, and (57.1±4.0)·10³ for the experimental group receiving the complex, p<0.05.

AFP and compound 2a exhibit no immunogenic activity. At the same time a complex of AFP/Compound 2a (1:100) displayed marked immunostimulating action. Thus, the relative amount of AFC on the 5-th day after injection of the complex increased by 77%, and total AFC amount increased by 43% in comparison with amount of cells in the animals immunized only with sheep erythrocytes.

Example 40

The Influence of a Complex of HumanAFP/Compound 10 (1:200) on Humoral Immune Response 0.15 ml of AFP/Compound 10 complex (1:200) was administered intravenously to 6 male mice of C57B1/6 line (weight 18–22 g) in the dose of 9 µg of AFP and 91 µg of compound 10 per capita. Simultaneously, a suspension of 5·10⁷ sheep erythrocytes was injected intraperitoneally (0.2 ml per capita). In the group receiving compound 10 mice were injected intravenously by one in the dose of 91 µg. Animals in the group with AFP received 9 µg of AFP. Mice in the control group were injected intravenously with an equal volume of saline. The effect of the AFP/Compound 10 complex on humoral immune response was analyzed by counting the quantity of AFC in the spleen according to Cunningham (per $10^6$ spleen cells and per spleen).

The relative amount of AFC on the 5-th day after injection was 273.3±20.4 for the control animals, 275.8±12.3 for the experimental group with AFP, p>0.05, 326.2±65.4 for the group with compound 10 alone, p>0.05, and 513.6±89.9 for experimental group with the complex, p<0.05. The total AFC amount was (31.3±2.5)·10³ for the control group, (33.6±2.1)·10³ for the experimental group with AFP, p>0.05, (34.7±8.5)·10³ for group with compound 10 alone, p>0.05, and (55.9±9.6)·10³ for the experimental group receiving the complex, p<0.05.

AFP and compound 10 alone exhibit no immunogenic activity. At the same time AFP/Compound 10 complex (1:200) displayed expressed immunostimulating action. Thus, the relative amount of AFC on the 5-th day after injection of AFP/Compound 10 complex (1:200) increased by 88%, and the total AFC amount increased by 79% in comparison with the amount of cells in the animals immunized only with sheep erythrocytes.

Example 41

The Influence of Human AFP/Compound 14 Complex (1:200) on Humoral Immune Response 0.15 ml of AFP/Compound 14 complex (1:200) was administered intravenously to 6 male mice of C57B1/6 line (weight 18–22 g) in the dose of 9 µg of AFP and 91 µg of compound 14 per capita. Simultaneously, a suspension of 5·10⁷ sheep erythrocytes was injected intraperitoneally (0.2 ml per capita). In the group with compound 14 mice were injected intravenously by one in the dose of 91 µg. Animals of group with AFP received 9 µg of AFP. Mice in the control group were injected intravenously with an equal volume of saline. The effect of the AFP/Compound 14 complex on humoral immune response was analyzed by counting the quantity of AFC in the spleen according to Cunningham (per $10^6$ spleen cells and per spleen).

The relative amount of AFC on the 5-th day after injection was 622.3±19.1 for the control animals, 573.3±63.6 for the experimental group receiving AFP, $p>0.05$, 645.8±64.4 for the group receiving compound 14 alone, $p>0.05$, and 967.3±44.7 for the experimental group receiving the complex, $p<0.05$. The total AFC amount was $(71.9±12.0) \cdot 10^3$ for the control group, $(69.8±14.2) \cdot 10^3$ for the experimental group receiving AFP, $p>0.05$, $(80.8± 12.7) \cdot 10^3$ for the group receiving compound 14 alone, $p>0.05$, and $(10.1±9.7) \cdot 10^3$ for the experimental group receiving the complex, $p<0.05$.

AFP and compound 14 alone exhibit no immunogenic activity. At the same time AFP/Compound 14 complex (1:200) displayed marked immunostimulating action. Thus, the relative amount of AFC on the 5-th day after injection of AFP/Compound 14 complex (1:200) increased by 55%, and total AFC amount increased by 53% in comparison with amount of cells in the animals immunized only with sheep erythrocytes.

Example 42

The Influence of Rat AFP/Compound 7 Complex (1:200) on Humoral Immune Response 0.15 ml of AFP/Compound 7 complex (1:200) was administered intravenously to 6 male mice of C57B1/6 line (weight 18–22 g) in the dose of 9 µg of AFP and 91 µg of compound 7 per capita. Simultaneously, a suspension of 5·10⁷ sheep erythrocytes was injected intraperitoneally (0.2 ml per capita). In the group with compound 7 mice were injected intravenously by one in the dose of 91 µg. Animals of group with AFP received 9 µg of AFP. Mice of control group were injected intravenously with equal volume of saline. AFP/Compound 7 complex effect on humoral immune response was analyzed by counting the quantity of AFC in the spleen according to Cunningham (per $10^6$ spleen cells and per spleen).

The relative amount of AFC on the 5-th day after injection was 498.6±26.3 for control animals, 521.4±49.1 for the experimental group receiving AFP, $p>0.05$, 574.9±39.6 for the group receiving compound 7 alone, $p>0.05$, and 743.9±65.4 for the experimental group receiving the complex, $p<0.01$. The total AFC amount was $(56.1±4.3) \cdot 10^3$ for the control group, $(59.7±5.1) \cdot 10^3$ for the experimental group receiving AFP, $p>0.05$, $(60.4±5.4) \cdot 10^3$ for the group receiving compound 7 alone, $p>0.05$, and $(82.7±9.7) \cdot 10^3$ for the experimental group receiving the complex, $p<0.05$.

AFP and compound 7 alone exhibit no immunogenic activity. At the same time AFP/Compound 7 complex (1:200) displayed marked immunostimulating action. Thus, the relative amount of AFC on the 5-th day after injection of AFP/Compound 7 complex (1:200) increased by 49%, and total AFC amount increased by 47% in comparison with amount of cells in the animals immunized only with sheep erythrocytes.

Example 43

The Influence of Rat AFP/Compound 15 Complex (1:200) on Humoral Immune Response 0.15 ml of AFP/Compound 15 complex (1:200) was administered intravenously to 6 mice males of C57B1/6 line (weight 18–22 g) in the dose of 9 µg of AFP and 91 µg of compound 15 per capita. Simultaneously, a suspension of 5·10⁷ sheep erythrocytes was injected intraperitoneally (0.2 ml per capita). In the group receiving compound 15, the mice were injected intravenously by one in the dose of 91 µg. Animals in the AFP-group received 9 µg of AFP. Mice in the control group were injected intravenously with an equal volume of saline. The effect of the AFP/Compound 15 complex on humoral immune response was analyzed by counting the quantity of AFC in the spleen according to Cunningham (per $10^6$ spleen cells and per spleen).

The relative amount of AFC on the 5-th day after injection was 556.8±32.2 for the control animals, 507.2±27.5 for the experimental group receiving AFP, $p>0.05$, 594.7±41.4 for the group receiving compound 15 alone, $p>0.05$, and 837.4±69.3 for the experimental group receiving the complex, $p<0.01$. The total AFC amount was $(66.7±5.4) \cdot 10^3$ for control group, $(64.6±6.8) \cdot 10^3$ for the experimental group receiving AFP, $p>0.05$, $(70.8±8.2) \cdot 10^3$ for the group receiving compound 15 alone, $p>0.05$, and $(99.0±10.1) \cdot 10^3$ for the experimental group receiving the complex, $p<0.05$.

AFP and compound 15 alone exhibit no immunogenic activity. At the same time AFP/Compound 15 complex (1:200) displayed marked immunostimulating aefion. Thus, the relative amount of AFC on the 5-th day after injection of AFP/Compound 15 complex (1:200) increased by 50%, and total AFC amount increased by 48% in comparison with amount of cells in the animals immunized only with sheep erythrocytes.

Example 44

The Influence of Rat AFP/Compound 1 Complex (1:100) on Humoral Immune Response 0.15 ml of AFP/Compound 1 complex was administered intravenously to 6 mice males of C57B1/6 line (weight 18–22 g) in the dose of 9 µg of AFP and 45.5 µg of compound 1 per capita. Simultaneously, a suspension of 5·10⁷ sheep erythrocytes was injected intraperitoneally (0.2 ml per capita). In the group with compound 1 mice were injected intravenously by one in the dose of 45.5 µg. Animals of group with AFP received 9 µg of AFP. Mice in the control group were injected intravenously with an equal volume of saline. Complex AFP/Compound 1 effect on humoral immune response was analyzed by counting the quantity of AFC in the spleen according to Cunningham (per $10^6$ spleen cells and per spleen).

The relative amount of AFC on the 5-th day after injection was 374.5±19.2 for the control animals, 346.1±26.8 for the experimental group receiving AFP, $p>0.05$, 413.1±31.5 for the group receiving compound 1, $p>0.05$, and 585.0±51.7 for the experimental group receiving AFP/Compound 1 complex, $p<0.01$. The total AFC amount was $(35.8±3.6) \cdot 10^3$ for the control group, $(34.1±3.3) \cdot 10^3$ for the experimental group receiving AFP, $p>0.05$, $(38.4±3.7) \cdot 10^3$ for the group receiving compound 1 alone, $p>0.05$, and $(51.2±4.1) \cdot 10^3$ for the experimental group receiving complex, $p<0.05$.

AFP and compound 1 alone exhibit no immunogenic activity. At the same time AFP/Compound 1 complex (1:100) displayed marked immunostimulating action. Thus, the relative amount of AFC on the 5-th day after injection of the complex increased by 56%, and total AFC amount increased by 43% in comparison with amount of cells in the animals immunized only with sheep erythrocytes.

Example 45

Preparation of a Complex of the Compounds 1 through 4, 1a through 4a, and 5 through 20, with AFP 20 mg AFP (0.3 μmol) was dissolved in 150 ml saline solution. 30 mg any compound (1–4, 1a–4a, 5–16) was dissolved in 5 ml saline solution and was added to the obtained AFP solution. The mixture was incubated for 30 min at room temperature (20–25° C.). The obtained complex was concentrated to 10 ml using Sartocon® Micro Unit (Sartorius) for high-molecular weight compounds with a 20 000 Da membrane cut off. The final solution was sterilized with a syringe tip Minisart®-SRP Syringe Filter (Sartorius) a membrane of 22μ pore size. A sterilized concentrated preparation was distributed in 10 vials of 1 ml each. Vials were blown with argon stream, closed firmly and stored at 4–8° C.

Example 46

AFP Binding with Compounds 1–4, 1a–4a, and 5–20

In order to determine the affinity human of AFP to compounds 1 through 4, 1a through 4a, and 5 through 20, a competitive substitution of [5,6,8,9,11,12,14,15-$^3$H] arachidonic acid from the protein's binding site was used. To tubes containing 0.05 mmol AFP in 1 ml 0.1 M bicarbonate buffer and 0.7 pmol [$^3$H]arachidonic acid and increasing amounts (5–5000 pmol) of arachidonic acid or any one of the title compounds 1–4, 1a–4a, and 5–20 were added. The tubes were incubated for 2 hr at room temperature. To separate protein-bound and free fractions of [$^3$H] arachidonic acid, tubes were incubated at 4° C. for 15 min with dextran covered activated carbon (0.5% suspension). The carbon was sedimented by centrifugation at 3000×g, aliquotes were added to 10 ml scintillating mixture and the vials were measured in a beta-counter.

The binding parameters of arachidonic acid and the compounds (1–4, 1a–4a, 5–16) the number of binding sites per protein molecule were calculated according to Scatchard (Scatchard O., Ann.N.Y.Acad.Sci. 51., p 660–664, 1949), and Blondeau (Blondeau J.-P., et al., Steroids, V. 32, N 5, P. 563–575, 1978).

Based on three independent determinations; the $K_a$ value for AFP with arachidonic acid was found to be $6 \cdot 10^7$ M$^{-1}$ and n>1.2. For the title compounds 1 through 4, 1a through 4a, and 5 through 20, the inhibition equilibrium association constants ($K_i$) were in the interval of $0.9 \cdot 10^6$ M$^{-1}$–$4 \cdot 10^6$ M$^{-1}$.

Example 47

Determination the Molecular Weight of Complexes Human AFP with Title Compounds

In order to determine the molar ratio between AFP and the compounds 1–4, 1a–4a, and 5–20 in complexes, ultrafiltration and/or gel-filtration chromatography was performed. The detection of complexes was carried out by measuring the absorbance at 280 nm and 345 nm and counting to determine, if the radioactive label [$^{125}$I] had been incorporated into the AFP molecule and [$^3$H] into compounds 5–8 ([$^3$H] arachidonic acid was used in synthesis).

The present inventor carried out gel exclusion chromatography of AFP complexes with compounds 1–4, 1a–4a, and 5–20 at different amounts of components—1 mole AFP per 700, 1400 and 2100 moles of the compound, for estimation of the AFP maximum binding capacity. The data obtained indicate that the ratio AFP/compound in complexes is between 1/100 and 1/300. In addition, these molar ratios AFP/compound in the complexes depend on the initial amounts of compounds in the solution. Thus, initial amounts of 1 mole AFP per 700 moles of the compound gives a ratio close to 1/100 (AFP/compound) in the complex; amounts of 1 mole AFP per 1400 moles of the compound gives a ratio close to 1/200 (AFP/compound) in the complex; amounts of 1 mole AFP per 2100 moles of the compound gives a ratio close to 1/300 (AFP/compound) in the complex.

The synthesis scheme can be outlined as below:

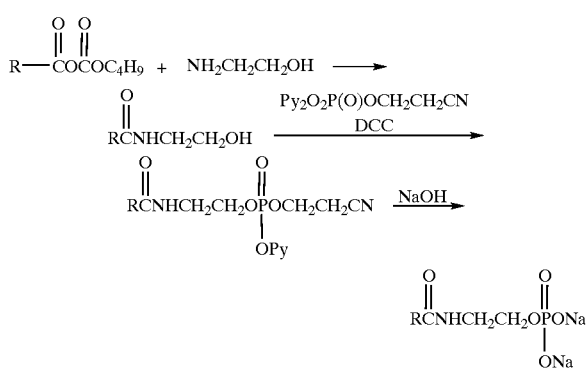

where R is:

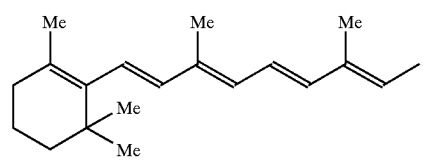

(1)

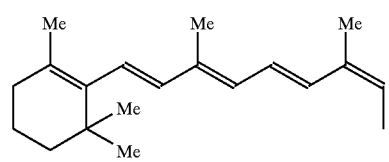

(1a)

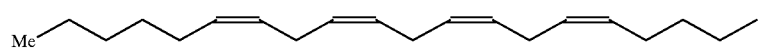

(5)

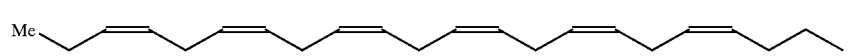

(9)

-continued
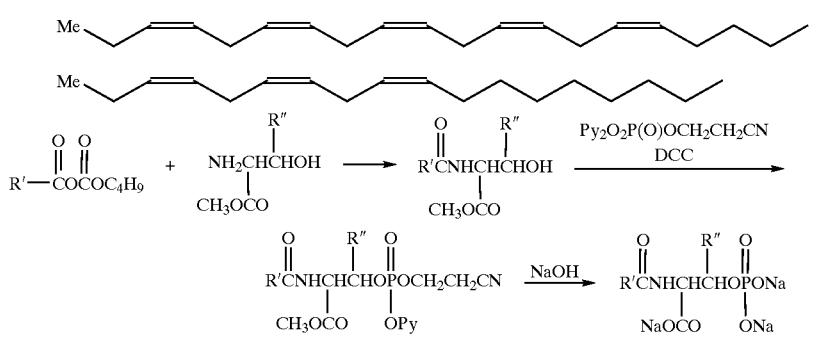
where R is:
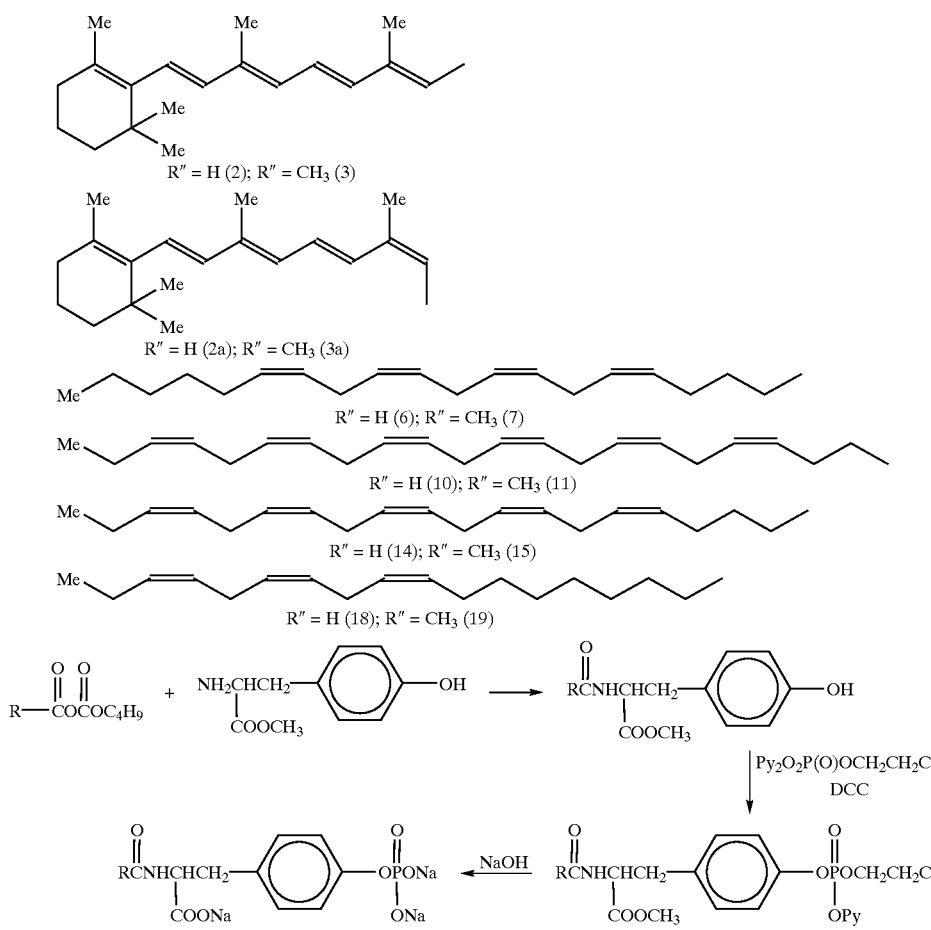
where R is
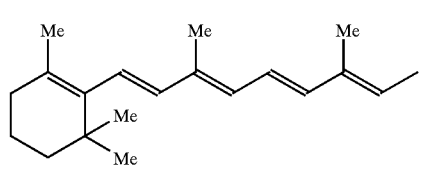

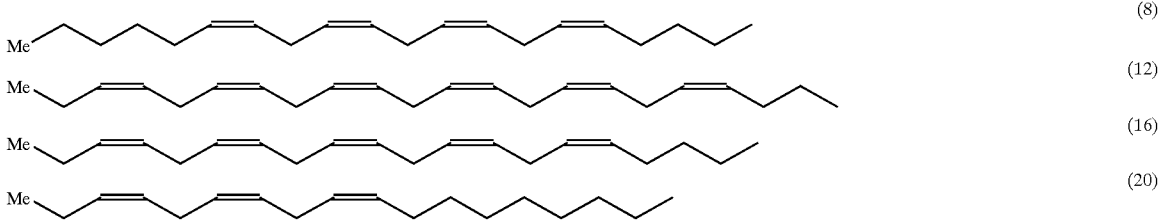

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto.

What is claimed is:

1. A complex of alpha-fetoprotein (AFP) and a compound having the following formula

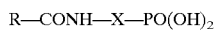

wherein R is independently selected from

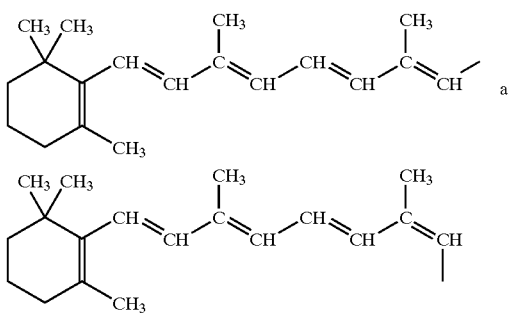

and $CH_3(CH_2)_4(CH=CH-CH_2)_4CH_2CH_2-$
and $CH_3(CH_2CH=CH)_6CH_2CH_2-$
and $CH_3(CH_2CH=CH)_5(CH_2)_3-$
and $CH_3(CH_2CH=CH)_3(CH_2)_7-$ and where X is independently selected from —$CH_2$—$CH_2$—
and —$CH(CO_2H)$—$CH_2$—
and —$CH(CO_2H)$—$CH(CH_3$—
and —$CH(CO_2H)$—$CH_2$—$C_6H_5$—.

2. A complex comprising alpha-fetoprotein and a compound selected from the group consisting of:

N-(all-trans-retinoyl)-o-phospho-2-aminoethanol,
N-(13-cis-retinoyl)-o-phospho-2-aminoethanol,
N-(all-trans-retinoyl)-o-phospho-L-serine,
N-(13-cis-retinoyl)-o-phospho-L-serine,
N-(all-trans-retinoyl)-o-phospho-L-threonine,
N-(13-cis-retinoyl)-o-phospho-L-threonine,
N-(all-trans-retinoyl)-o-phospho-L-tyrosine, and
N-(13-cis-retinoyl)-o-phospho-L-tyrosine.

3. A complex comprising alpha-fetoprotein and a compound selected from the group consisting of:

N-linolenoyl-o-phospho-2-aminoethanol,
N-linolenoyl-o-phospho-L-serine,
N-linolenoyl-o-phospho-L-threonine, and
N-linolenoyl-o-phospho-L-tyrosine.

4. A complex comprising alpha-fetoprotein and a compound selected from the group consisting of:

N-docosahexaenoyl-o-phospho-2-aminoethanol,
N-docosahexaenoyl-o-phospho-L-serine,
N-docosahexaenoyl-o-phospho-L-threonine, and
N-docosahexaenoyl-o-phospho-L-tyrosine.

5. A complex comprising alpha-fetoprotein and a compound selected from the group consisting of:

N-eicosapentaenoyl-o-phospho-2-aminoethanol,
N-eicosapentaenoyl-o-phospho-L-serine,
N-eicosapentaenoyl-o-phospho-L-threonine, and
N-eicosapentaenoyl-o-phospho-L-tyrosine.

6. A complex comprising alpha-fetoprotein and a compound selected from the group consisting of:

N-arachidonoyl-o-phospho-2-aminoethanol,
N-arachidonoyl-o-phospho-L-serine,
N-arachidonoyl-o-phospho-L-threonine, and
N-arachidonoyl-o-phospho-L-tyrosine.

7. A complex according to claim 1 wherein the complex is an equilibrium reversible complex wherein the concentration of said compound is at least equal to the critical micelle concentration of said complex.

8. A complex according to claim 2 wherein the complex is an equilibrium reversible complex wherein the concentration of said compound is at least equal to the critical micelle concentration of said complex.

9. A complex according to claim 3 wherein the complex is an equilibrium reversible complex wherein the concentration of said compound is at least equal to the critical micelle concentration of said complex.

10. A complex according to claim 4 wherein the complex is an equilibrium reversible complex wherein the concentration of said compound is at least equal to the critical micelle concentration of said complex.

11. A complex according to claim 5 wherein the complex is an equilibrium reversible complex wherein the concentration of said compound is at least equal to the critical micelle concentration of said complex.

12. A complex according to claim 6 wherein the complex is an equilibrium reversible complex wherein the concentration of said compound is at least equal to the critical micelle concentration of said complex.

13. A complex according to claim 1 wherein the complex is an equilibrium reversible complex wherein the concentration of said compound is 100 to 300 moles per mole alpha-fetoprotein in said complex.

14. A complex according to claim 2 wherein the complex is an equilibrium reversible complex wherein the concentration of said compound is 100 to 300 moles per mole alpha-fetoprotein in said complex.

15. A complex according to claim 3 wherein the complex is an equilibrium reversible complex wherein the concentration of said compound is 100 to 300 moles per mole alpha-fetoprotein in said complex.

16. A complex according to claim 4 wherein the complex is an equilibrium reversible complex wherein the concentration of said compound is 100 to 300 moles per mole alpha-fetoprotein in said complex.

17. A complex according to claim 5 wherein the complex is an equilibrium reversible complex wherein the concentration of said compound is 100 to 300 moles per mole alpha-fetoprotein in said complex.

18. A complex according to claim 6 wherein the complex is an equilibrium reversible complex wherein the concentration of said compound is 100 to 300 moles per mole alpha-fetoprotein in said complex.

19. A pharmaceutical composition comprising at least one complex according to claim 1.

20. A pharmaceutical composition comprising at least one complex according to claim 2.

21. A pharmaceutical composition comprising at least one complex according to claim 3.

22. A pharmaceutical composition comprising at least one complex according to claim 4.

23. A pharmaceutical composition comprising at least one complex according to claim 5.

24. A pharmaceutical composition comprising at least one complex according to claim 6.

25. A method for the treatment of cancer comprising administering a complex according to claim 1 to a patient.

26. A method for the treatment of cancer comprising administering a complex according to claim 2 to a patient.

27. A method for the treatment of cancer comprising administering a complex according to claim 3 to a patient.

28. A method for the treatment of cancer comprising administering a complex according to claim 4 to a patient.

29. A method for the treatment of cancer comprising administering a complex according to claim 5 to a patient.

30. A method for the treatment of cancer comprising administering a complex according to claim 6 to a patient.

* * * * *

UNITED STATES PATENT AND TRADEMARK OFFICE
CERTIFICATE OF CORRECTION

PATENT NO.    : 6,403,554 B2
DATED         : June 11, 2002
INVENTOR(S)   : Oleg Strelchenok It is certified that error appears in the above-identified patent and that said Letters Patent is hereby corrected as shown below:

Column 39,
Line 23, reads: "R-CONH-X-PO(OH)$_2$" should read -- R-CONH-X-OPO(OH)$_2$ --.

Signed and Sealed this

Twenty-sixth Day of November, 2002

Attest:

Attesting Officer

JAMES E. ROGAN
Director of the United States Patent and Trademark Office